US010893825B2

(12) United States Patent
Dieffenderfer et al.

(10) Patent No.: US 10,893,825 B2
(45) Date of Patent: Jan. 19, 2021

(54) SYSTEM AND METHOD OF MONITORING RESPIRATORY PARAMETERS

(71) Applicant: North Carolina State University, Raleigh, NC (US)

(72) Inventors: James P. Dieffenderfer, Raleigh, NC (US); Mike A. Brown, Raleigh, NC (US); Leigh M. Johnson, Raleigh, NC (US); John F. Muth, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 818 days.

(21) Appl. No.: 15/115,401

(22) PCT Filed: Jan. 31, 2015

(86) PCT No.: PCT/US2015/014005
§ 371 (c)(1),
(2) Date: Jul. 29, 2016

(87) PCT Pub. No.: WO2015/117046
PCT Pub. Date: Aug. 6, 2015

(65) Prior Publication Data
US 2017/0007159 A1    Jan. 12, 2017

Related U.S. Application Data

(60) Provisional application No. 61/934,415, filed on Jan. 31, 2014.

(51) Int. Cl.
*A61B 5/097* (2006.01)
*A61B 5/00* (2006.01)
(Continued)

(52) U.S. Cl.
CPC .............. *A61B 5/097* (2013.01); *A61B 5/082* (2013.01); *A61B 5/087* (2013.01); *A61B 5/0871* (2013.01);
(Continued)

(58) Field of Classification Search
None
See application file for complete search history.

(56) References Cited

U.S. PATENT DOCUMENTS 3,577,984 A    5/1971    Levy et al.
3,621,835 A    11/1971   Sukuzi et al.
(Continued)

FOREIGN PATENT DOCUMENTS

CN    102525478    4/2012

OTHER PUBLICATIONS

"Forced Expiratory Volume and Forced Vital Capacity", Dec. 9, 2012, University of Michigan Health System, https://web.archive.org/web/20121209120518/https://www.uofmhealth.org/health-library/aa73564.*

(Continued)

*Primary Examiner* — Jacqueline Cheng
*Assistant Examiner* — Jairo H Portillo
(74) *Attorney, Agent, or Firm* — Michael Best & Friedrich LLP

(57) ABSTRACT

A spirometer includes a housing, a mouthpiece coupled to the housing, and a measurement unit. The measurement unit is configured to receive air expelled by a user, and generate an electrical quantity corresponding to a peak expiratory flow or a forced expiratory volume based on the expelled air. The spirometer also includes a processing module supported by the housing, and configured to receive the electrical quantity from the measurement unit, a display coupled to the measurement unit to display an indication of the peak
(Continued)

expiratory flow or the forced expiratory volume, and an energy harvester. The energy harvester is coupled to the measurement unit and the processing module, and is configured to receive energy from one of a group consisting of the measurement unit and an energy sensor, store the received energy in an energy storage device, and transfer the energy to the processing module.

22 Claims, 15 Drawing Sheets

(51) Int. Cl.
    *A61B 5/087*     (2006.01)
    *A61B 5/08*     (2006.01)
    *A61B 5/09*     (2006.01)
    *A61B 10/00*     (2006.01)

(52) U.S. Cl.
    CPC .............. *A61B 5/09* (2013.01); *A61B 5/6898* (2013.01); *A61B 5/743* (2013.01); *A61B 2010/0087* (2013.01); *A61B 2560/0209* (2013.01); *A61B 2560/0214* (2013.01); *A61B 2560/045* (2013.01); *A61B 2562/0219* (2013.01)

(56) References Cited

U.S. PATENT DOCUMENTS

| | | | | |
|---|---|---|---|---|
| 3,680,378 | A * | 8/1972 | Aurilio | A61B 5/09 73/861.77 |
| 3,922,525 | A * | 11/1975 | Kozak | A61B 5/09 250/231.16 |
| 4,282,883 | A | 8/1981 | Yerushalmy | |
| 5,137,026 | A | 8/1992 | Waterson et al. | |
| 5,158,094 | A | 10/1992 | Miller | |
| 5,277,195 | A | 1/1994 | Williams | |
| 5,522,380 | A | 6/1996 | Dwork | |
| 5,647,370 | A | 7/1997 | Harnoncourt | |
| 5,724,986 | A | 3/1998 | Jones et al. | |
| 5,740,795 | A * | 4/1998 | Brydon | A61M 16/024 128/204.18 |
| 5,749,368 | A * | 5/1998 | Kase | A61B 5/0871 482/13 |
| 5,816,246 | A | 10/1998 | Mirza | |
| 6,126,613 | A * | 10/2000 | Edwards | A61B 5/09 600/538 |
| 6,322,519 | B1 | 11/2001 | Moulin | |
| 7,867,172 | B1 | 1/2011 | Baruti | |
| 8,034,002 | B2 | 10/2011 | Coifman | |
| 2004/0039295 | A1 | 2/2004 | Olbrich et al. | |
| 2007/0149891 | A1* | 6/2007 | George | A61B 5/0813 600/533 |
| 2010/0242960 | A1* | 9/2010 | Zangerle | A61M 15/0065 128/203.15 |
| 2010/0324455 | A1* | 12/2010 | Rangel | A43B 7/147 600/592 |
| 2011/0152707 | A1 | 6/2011 | Jang | |
| 2012/0029376 | A1* | 2/2012 | Meng | A61B 5/087 600/538 |
| 2012/0226111 | A1 | 9/2012 | Leboeuf et al. | |
| 2012/0234323 | A1* | 9/2012 | Connor | A61M 16/0066 128/204.21 |
| 2013/0053719 | A1 | 2/2013 | Wekell | |
| 2013/0217979 | A1* | 8/2013 | Blackadar | A61B 5/0024 600/301 |
| 2013/0324788 | A1 | 12/2013 | Holley et al. | |
| 2014/0316296 | A1 | 10/2014 | Meng et al. | |
| 2017/0007159 | A1 | 1/2017 | Dieffenderfer et al. | |

OTHER PUBLICATIONS

"Guide Rail." Merriam-Webster.com. Merriam-Webster, n.d. Web. Sep. 27, 2018.*
Adopted bluetooth 5 core specifications, Bluetooth Technology Website, webpage available as early as Mar. 5, 2012, https://www.bluetooth.org/Technical/Specifications/adopted.htm.
Akinbami, L. et al., "Asthma Prevalence, Health Care Use, and Mortality: United States, 2005-2009," National Center for Health Statistics, 2011.
Allergy and Asthma Mothers of Asthmatics (AANMA) website available as early as Aug. 27, 2011, http://www.asthmacommunitynetwork.org/node/2547.
Alliance Tech Medical, website available as early as Sep. 16, 2013, http://alliancetechmedical.com/products/spirometers/.
American Academy of Allergy, Asthma & Immunology (AAAAI). (2012). Asthma Statistics. Retrieved from www.aaaai.org/about-the-aaaai/newsroom/asthma-statistics.aspx.
American Academy of Allergy, Asthma and Immunology website available as early as Jul. 29, 2011, http://www.aaaai.org/home.aspx.
American College of Allergy, Asthma & Immunology. (2012). Asthma Facts. Retrieved from www.acaai.org/allergist/news/Pages/Asthma_Facts.aspx.
American Lung Association. (2011). Asthma in Adults and Children's Fact Sheets. Retrieved from www.lung.org/.
American Lung Association. (2011).Trends in COPD (Chronic Bronchitis and Emphysema): Morbidity and Mortality. Retrieved from www.lung.org/finding-cures/our-research/trend-reports/copd-trend-report.pdf.
American Lung Association. (2012). Trends in Asthma Morbidity and Mortality. p. 14. Retrieved from www.lung.org/finding-cures/our-research/trend-reports/asthma-trend-report.pdf.
AnActive Life website available as early as May 18, 2015, http://www.anactivelife.com/nebulizers-s/155.htm.
Assess Peak Flow Meter by Phillips, Medline Industries, Inc., website available as early as Sep. 13, 2013, https://www.medline.com/sku/item/MDPHDTHS740012;ecomsessionid=Uc0Gn7rs1jXalLdhycNIKg_?skuIndex=S1&question=&flowType=&indexCount=.
Asthma statistics. Retrieved from American Academy of Allergy Asthma and Immunology website: http://www.aaaai.org/about-the-aaaai/newsroom/asthma-statistics.aspx. Webpage available as early as Apr. 7, 2016.
Bluetooth transceiver module. (May 10, 2011). Retrieved from DigiPak website: http://digipak.org/?product=hc-09-bluetooth-module-_-sku-282.
Center for Disease Control. (2010). Lifetime Asthma Population Estimates by Age. Retrieved from www.cdc.gov/asthma/nhis/2010/table1-1.htm.
Clement Clarke website available as early as May 8, 1999, http://www.clement-clarke.com.
ESRI Business Analyst Online. (2011). Health and Beauty Market Potential. Retrieve from http://bao.esri.com.
Fox, S., & Duggan, M. (n.d.). Mobile Health 2012 | Pew Research Center's Internet & American Life Project. Pew Research Center's Internet & American Life Project. Retrieved Dec. 9, 2012, from http://pewinternet.org/Reports/2012/Mobile-Health.aspx.
Frost and Sullivan. (2011). U.S. Asthma/COPD Market. Retrieved from https://www.frost.com/prod/servlet/report-brochure.pag?id=N85C-01-00-00-00.
Frost and Sullivan. (2012). 2012 United States Medical Devices Outlook. Retrieve from www.frost.com.
GE Medical Systems and NBC Partner to Bring Patient Programming into hospitals; The Patient Channel to Help Patients, Families Better Understand Health Issues. Sep. 25, 2002. Retrieved from http://www.genewsroom.com/Press-Releases/GE-Medical-Systems-and-NBC-Partner-To-Bring-Patient-Programming-Into-Hospitals-The-Patient-Channel-To-Help-Patients-Families-Better-Understand-Health-Issues-265654.
Home Medical Equipment. Freedonia Group (2009). Retrieve from www.freedoniagroup.com.
International Search Report and Written Opinion for Application No. PCT/US2015/014005 dated Jun. 17, 2015 (18 pages).

(56) References Cited

OTHER PUBLICATIONS

Miller, Martin R. "The EU Peak Flow Meter: Historical Perspective, Why Change and What's Available." The Buyer's Guide to Respiratory Care Products. N.p., n.d. Web (2015).
nSpire Mechanical Pocket Peak Flow Meter from QuickMedical website available as early as Dec. 5, 2008, http://www.quickmedical.com/nspire/pocket_peak.html.
PC-Based Diagnostic Spirometry from nSpire website available as early as Jul. 21, 2001, http://www.nspirehealth.com/products/zan-100/.
Peak Flow Meters, Disposable Mouth Pieces & PFT Filters, retrieved from Mini Wright Peak Flow Meter website available as early as Oct. 21, 2013, http://miniwrightpeakflowmeter.com/index.html.
Personal Best Peak Flow Meter from Philips, website available as early as Sep. 28, 2015, http://www.usa.philips.com/healthcare/product/HCHS755012/personal-best-peak-flow-meter.
Personal Peak Flow Meter from Briggs Medical Service Company, 2010, http://www.mabisdmi.com/.
Personal Peak Flow Meter, Retrieved from Vitality Medical.com, website available as early as Apr. 6, 2011, http://www.vitalitymedical.com/respironics-personal-best-peak-flow-meter-low.html.
PF100 Asthma Monitor, Microlife Consumer Products, website available as early as Jun. 23, 2016, http://www.microlife.com/consumer-products/respiratory-care/asthma-monitor/pf-100.
PMD Healthcare, manufacturer of Spiro PD Personal Spirometer, announces support for Natinal COPD Awareness Month, Oct. 30, 2012, http://www.prweb.com/releases/personalspirometer/personalspirometry/prweb10065365.htm.
Product Index, Digi-Key Corporation. (Dec. 2012). Retrieved from http://www.digikey.com/product-search/en.
Professional Series (HT801) Retrieved from Home Care Technology, website available as early as Jan. 9, 2011, http://www.hometech.com.tw/HT801_detail.htm.
Rachelefsky, MD, G. Asthma guidelines and effective utilization of long-acting beta-agonists. (Jan. 10, 2012) Retrieved from Medscape Education website: http://www.medscape.org/viewarticle/537727.
Respiratory Care; Global Respiratory Care Devices Market 2010-2015. (May 16, 2011). Retrieved from www.lexisnexis.com/hottopics/Inacademic.
Respiratory Therapeutics Week. Global Respiratory Care Devices Market 2010-2015. (May 16, 2011) Retrieved from Lexis Nexis www.lexisnexis.com/hottopics/Inacademic.
Smith, Aaron. (Mar. 1, 2012) Nearly half of American adults are smartphone owners. Retrieved from Pew Internet. Retrieved from http://pewinternet.org/Reports/2012/Smartphone-Update-2012/Findings.aspx.
SpiroFlow Children's Peak Flow Meter Retrieved from Pocket Nurse website available as early as Jul. 3, 1998, http://www.pocketnurse.com/07/71/2350-spiroflow-peak-flow-meter-adult.
Spirometrics: Respiratory & Pulmonary Function (PFT) Supplies, Spiroflow PeakFlow Meter, website available as early as Jan. 8, 2000, http://www.spirometrics.com.
Strive Dual Zone Peak Flow Meter from Monaghan Medical website available as early as Jul. 21, 2001, https://www.monaghanmed.com/Strive-Peak-Flow-Meter.
Talking about nebulization method from Omron website available as early as Oct. 20, 2010, http://www.healthcare.omron.co.jp/english/overview/neu.html.
TruZone Peak Flow Meter, website available as early as Sep. 9, 2015, https://www.trudellmed.com/products/truzone.
Vitalograph micro spirometry, website available as early as Mar. 2, 2000, http://www.vitalograph.com/product/162436/micro.
Vitalograph Peak Flow Meter, website available as early as Feb. 3, 2008, http://www.medicaldevicedepot.com/Vitalograh-Asma-1-Electronic-Asthma-Monitor-p/40000.htm?dfw_tracker=3918-21850&gclid=CjwKEAjwh9PGBRCfso2n3ODgvUcSJAAhpW5ojX5Tllj0MxY1Lvx4n7t4xwAyCzIXdWdVDWOZ2J9F4BoC11Tw_wcB.
Vitalograph, Peak Flow Meters, website available as early as Mar. 2, 2000, https://vitalograph.com/products/8/peak-flow.
Woodruff, T., Barebones printed circuit boards. Retrieved from the Advanced Circuits website http://www.4pcb.com/bare-bones-pcbs/index.html. Webpage available as early as Nov. 3, 2012.

\* cited by examiner

SYSTEM AND METHOD OF MONITORING RESPIRATORY PARAMETERS

CROSS-REFERENCE TO RELATED APPLICATIONS

This application is a national stage filing under 35 U.S.C. § 371 of International Application No. PCT/US2015/014005, filed on Jan. 31, 2015, which is a non-provisional of and claims priority to U.S. Provisional Patent Application No. 61/934,415, filed on Jan. 31, 2014, the entire contents of which are incorporated herein by reference.

STATEMENT REGARDING FEDERALLY SPONSORED RESEARCH OR DEVELOPMENT

This invention was made with government support under grant 1160483 awarded by the National Science Foundation. The government has certain rights in the invention.

BACKGROUND OF THE INVENTION

Portable spirometry devices are often used by patients suffering from respiratory complications, such as chronic obstructive pulmonary disease (COPD).

SUMMARY OF THE INVENTION

The present invention relates to portable spirometry devices, such as portable devices capable of measuring certain respiratory parameters. The present invention is usable by anyone that desires to know or measure their respiratory data. While the invention may be discussed in the context of medical use, the invention is not limited to medical use, and may, for example, be used by athletes to monitor their respiratory data.

In one embodiment, the invention provides a spirometer comprising a housing, a mouthpiece coupled to the housing, a measurement module, a processing module, a display, and an energy harvester. The measurement module is configured to receive air expelled by a user, and generate an electrical quantity corresponding to a peak expiratory flow or a forced expiratory volume based on the expelled air. The processing module is supported by the housing, and configured to receive the electrical quantity from the measurement unit. The display is coupled to the measurement unit to display an indication of the peak expiratory flow or the forced expiratory volume. The energy harvester is coupled to the measurement unit and the processing module, the energy harvester configured to receive energy from one of a group consisting of the measurement unit and an energy device, store the received energy in an energy storage device, and transfer the energy to the processing module.

In another embodiment, the invention provides a spirometer comprising a housing, a mouthpiece coupled to the housing, a single circuit board supported by the housing, and including a sensing portion and a processing portion, a measurement module, a main measurement unit, an ambient sensor, a processing module, and a protector. The measurement module is coupled to the sensing portion, and includes the main measurement unit configured to receive air expelled by the user, and measure a pulmonary parameter of the user, the pulmonary parameter including a peak expiratory flow or a forced expiratory volume, and an ambient sensor coupled o the sensing portion, and configured to measure an ambient air parameter, wherein the parameter includes one of a group consisting of temperature, humidity, and concentration of a gas. The processing module is coupled to the processing portion, and configured to receive signals from the main measurement unit and the ambient sensor. The protector is coupled to the single circuit board, the protector configured to protect the processing portion and the processing module from one of a group consisting of the air expelled by the user and ambient air.

In a further embodiment, the invention provides a respiratory monitoring system comprising a spirometer and an external electronic device. The spirometer includes a housing, a mouthpiece coupled to the housing, a measurement unit configured to receive expelled air from a user, and generate an electrical quantity corresponding to a peak expiratory flow or a forced expiratory volume based on the expelled air, and a communication module configured to transmit a wireless message to an external electronic device including a pulmonary parameter based on the electrical quantity, the pulmonary parameter corresponding to the peak expiratory flow or the forced expiratory volume. The external electronic device includes a display, and a processor configured to receive the pulmonary parameter from the communication module, analyze the pulmonary parameter from the communication module, and display a treatment action for the user based on the analyzed pulmonary parameter.

In yet another embodiment, the invention provides a spirometer comprising a housing comprising a first shell and a second shell, the housing defining an enclosed cavity having a first compartment and a second compartment, a single circuit board supported by the housing within one of the first compartment and the second compartment, the single circuit board including a measurement module and a processing module configured to measure respiratory parameters of a user, and an output port in electrical communication with the processing module, the output port configured for coupling to external equipment.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using other known means including direct connections, wireless connections, etc.

In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium) executable by one or more processing units, such as a microprocessor and/or application specific integrated circuits ("ASICs"). As such, it should be noted that a plurality of hardware and software based devices, as well as a plurality of different structural components may be utilized to implement the invention. For example, "servers" and "computing devices" described in the specification can include one or more processing units, one or more computer-readable medium modules, one or more input/output interfaces, and various connections (e.g., a system bus) connecting the components.

Figure 1:
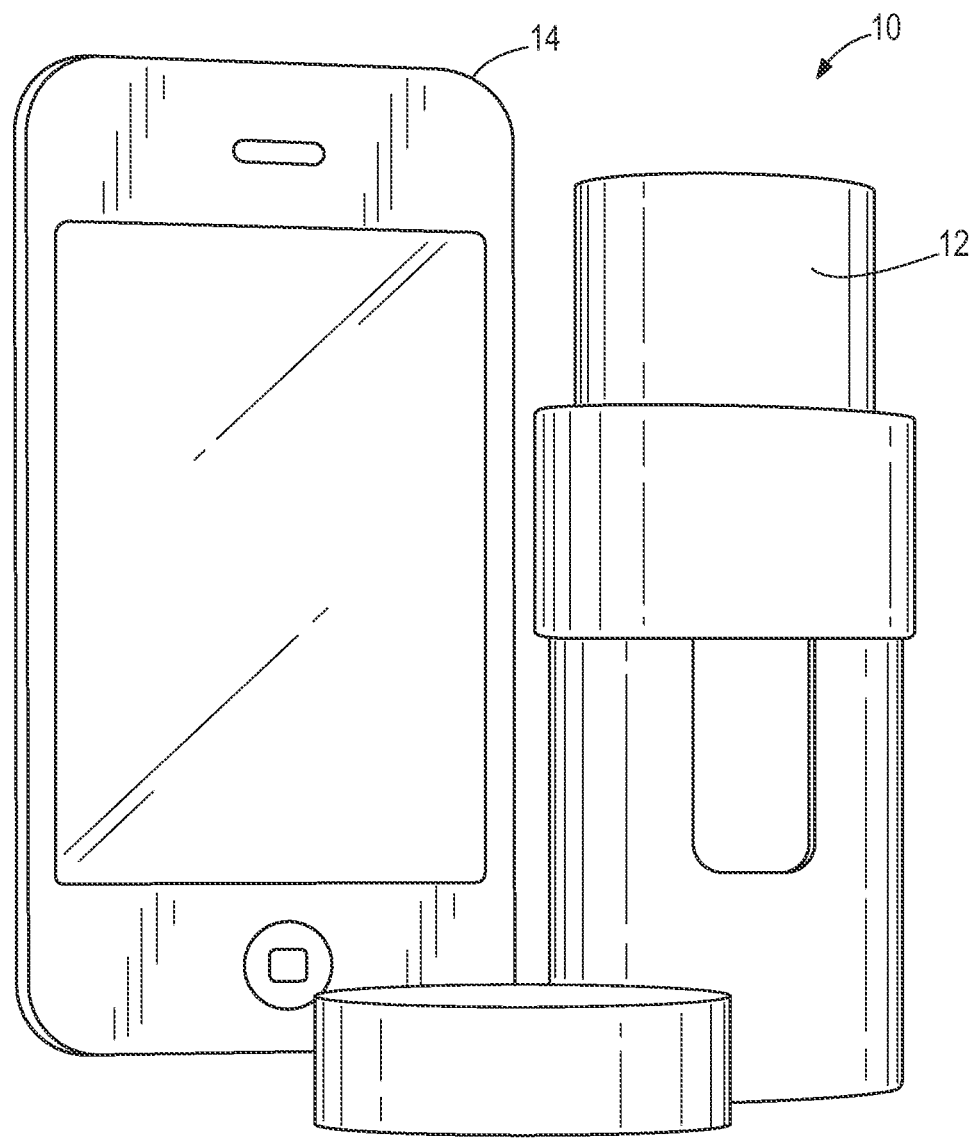
FIG. 1 illustrates a respiratory monitoring system according to one embodiment of the invention.

FIG. 1 illustrates a portable respiratory monitoring system 10. The system 10 can be used by individuals who suffer from asthma, chronic obstructive pulmonary disease (COPD), or other respiratory illnesses or conditions to measure lung capacity. The respiratory monitoring system 10 can also be accessed by physicians or personnel at medical care centers to receive updated information regarding patients and adjust treatments accordingly. Physicians can also use the system 10 as a spirometry device.

The system 10 includes a spirometer 12 and an external electronic device 14. The spirometer 12 measures one or more respiratory parameters associated with a patient. The respiratory parameter may be indicative of the user's lung health. The spirometer 12 then communicates with the electronic device 14 regarding the one or more measurements obtained through the spirometer 12. The electronic device 14 displays the measurements obtained from the spirometer 12 to a user (e.g., within a graphical user interface). In some embodiments, the electronic device 14 provides more information to the user regarding the measured pulmonary parameters. Through use of the respiratory system 10, the user can better manage their pulmonary health.

In some embodiments, the electronic device 14 includes a smart phone. For example, FIG. 1 illustrates the electronic device 14 as an Apple® iPhone. It should be understood, however, that other types of smart phones and other devices can be used as the electronic device 14. In particular, the electronic device 14 can include any type of device configured to communicate with the spirometer 12 over at least one connection (e.g., a wireless network) and display information received from the spirometer 12 on at least one display. Also, it should be understood that the electronic device 14 can be portable or mobile (e.g., designed to carried by the user), such as a smart phone or tablet, or non-portable (e.g., not generally designed to be carried by the user), such as a desktop computer.

As shown in FIG. 2, the spirometer 12 includes a housing 16, a mouthpiece 18, a cover 20, a front end measurement module 22, and a processing module 24. The housing 16 has an elliptical shape, which fits comfortably into the hand of a user and is appealing to the eye. The housing 16 includes a first body section 26 and a second body section 28. The first and the second body sections 26, 28 join together laterally (e.g., along a length L of the spirometer 12). Each body section 26, 28 includes an inner surface 30, an outer surface 32, a first edge 34, and a second edge 36. The first and second edges 34, 36 include a step 38. When the first body section 26 is permanently coupled to the second body section 28, the step 38 in each of the edges 34, 36 of each body section forms a first guide rail 40 and a second guide rail 41 (FIG. 3) along the length L of the housing 16. As shown in FIG. 3, the guide rails 40, 41 include a first notch 42 at the bottom of the housing 16 and a second notch 43 toward the middle of the housing 16. In other embodiments, the notches 42, 43 may be positioned elsewhere along the guiderails 40, 41. Referring back to FIG. 2, the first body section 26 includes a display 44 on its outer surface 32. The second body section 28 includes vents 46 on its outer surface 32.

Figure 4:
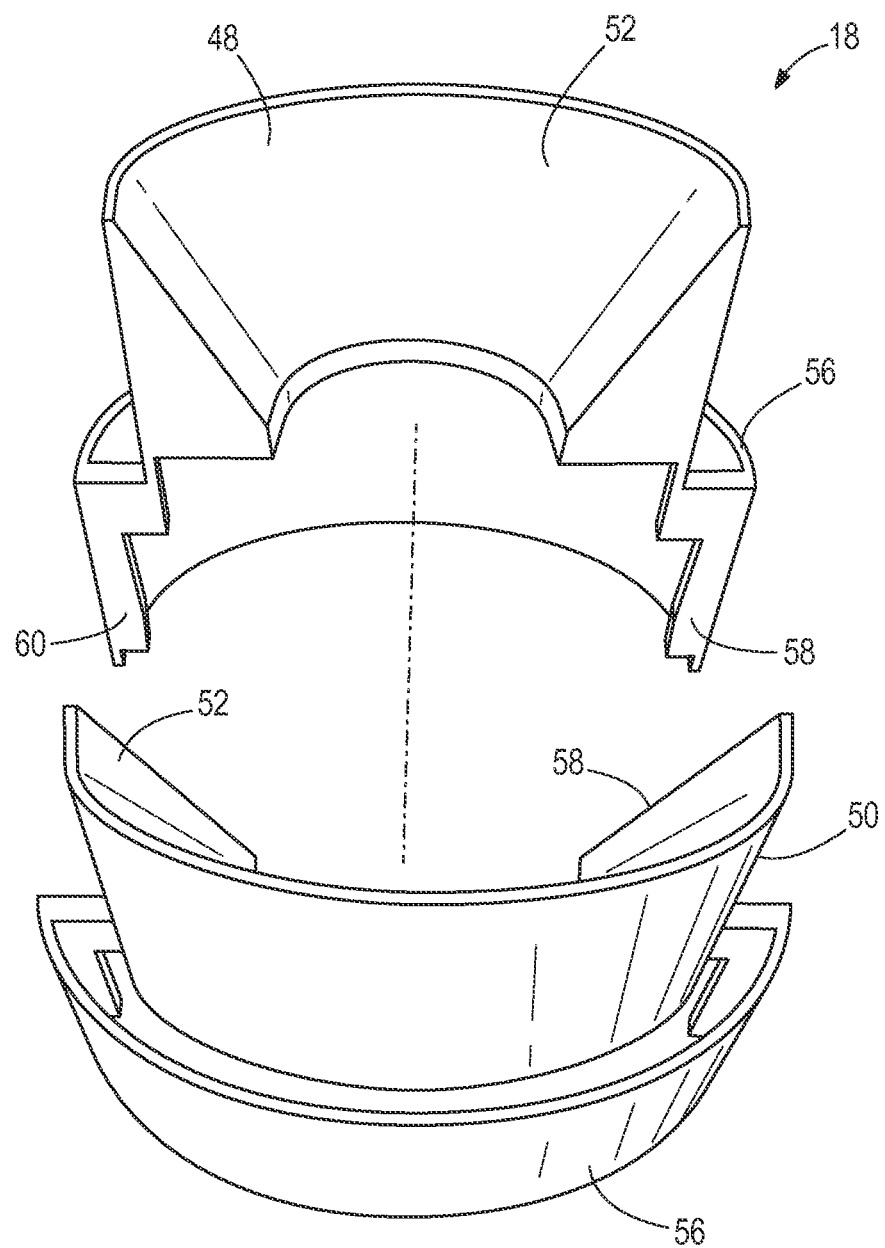
FIG. 4 shows the spirometer in the recessed position without the cover.
Figure 6:
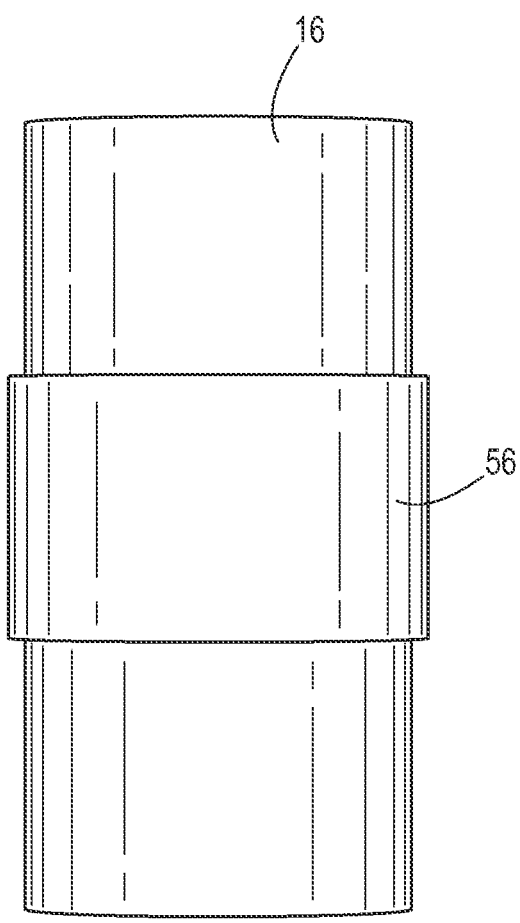
FIG. 6 is a top view of the spirometer while in the exposed position.
Figure 7:
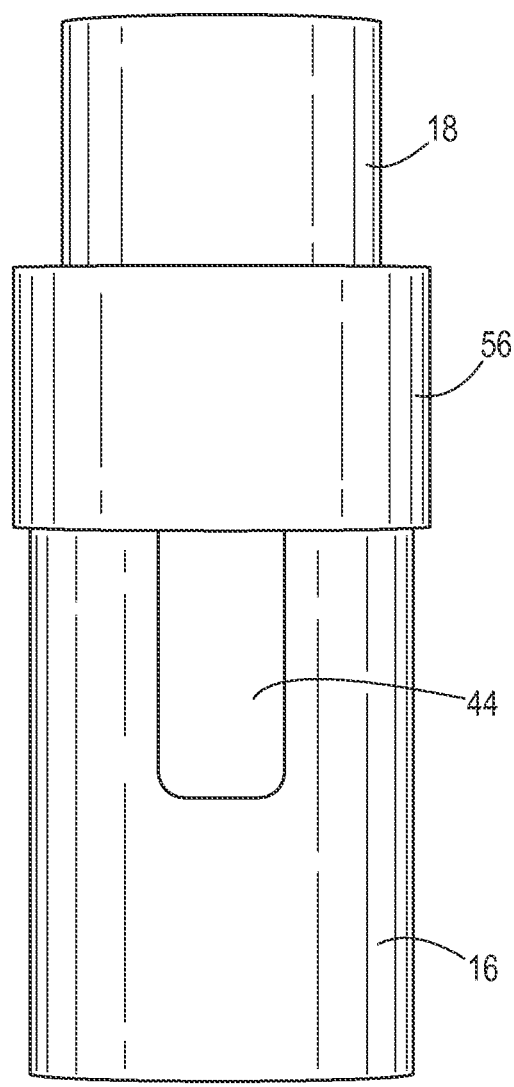
FIG. 7 is a side view of a housing of the spirometer.

As shown in FIG. 4, the mouthpiece 18 has an elliptical shape to match the shape of the housing 16. The mouthpiece 18 includes a first mouthpiece portion 48 and a second mouthpiece portion 50. The first and second mouthpiece portions 48, 50 join together to form the mouthpiece 18. Each mouthpiece portion 48, 50 includes an inner surface 52, and an outer surface 54. Each mouthpiece portion 48, 50 is also coupled to an outer ring 56. The outer ring 56 protrudes radially outward from the mouthpiece 18. The outer ring 56 coupled to each mouthpiece portion 48, 50 includes a first flange 58 and a second flange 60. The first flange 58 and the second flange 60 engage the guide rails 40, 41 in the housing 16. As shown in FIG. 4, the inner surface 52 of each mouthpiece portion 48, 50 is funnel shaped to increase the comfort of the use and to direct airflow into the spirometer 12.

Figure 5:
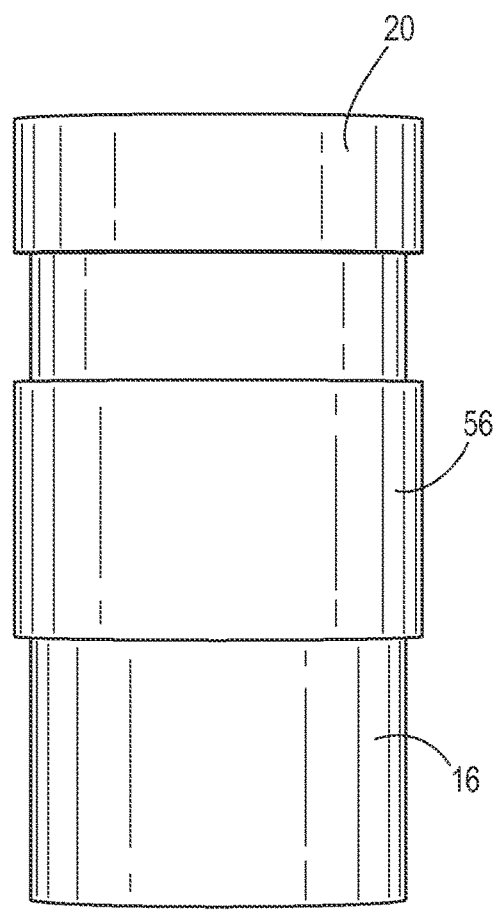
FIG. 5 shows the spirometer in an exposed position.
Figure 8:
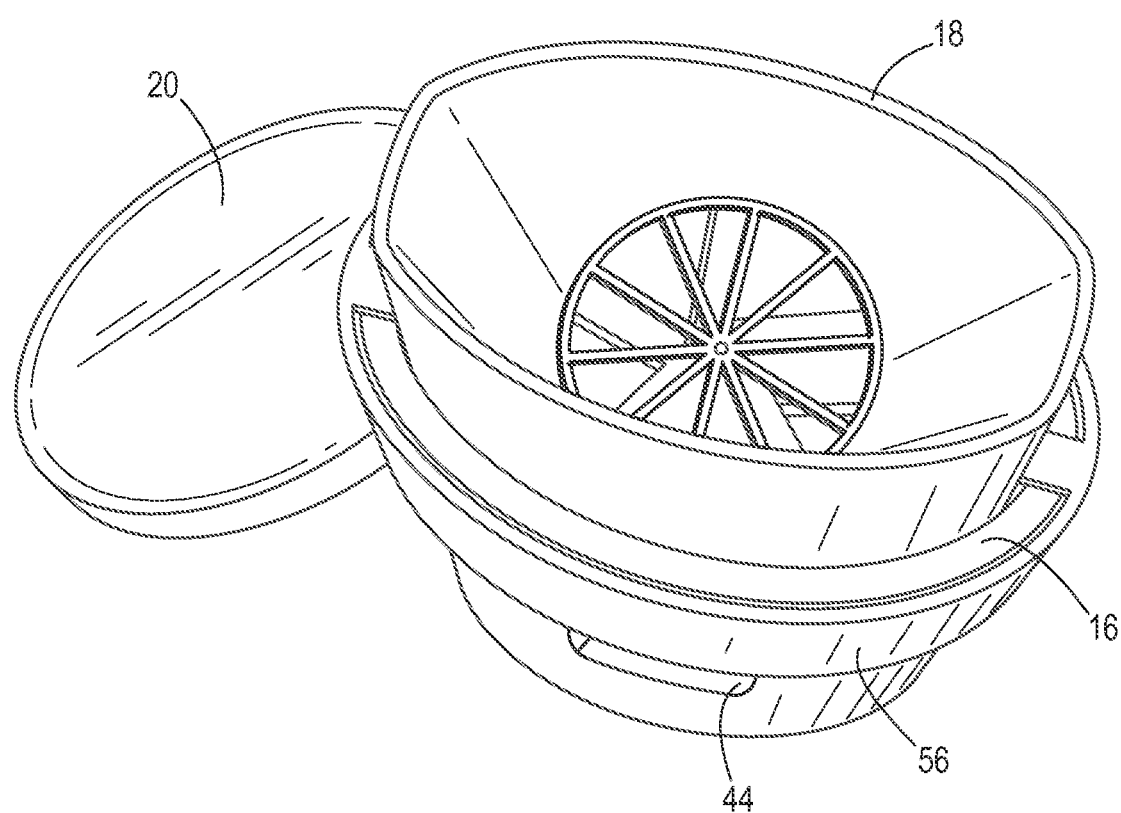
FIG. 8 is a top perspective view of a mouthpiece of the spirometer.

In the illustrated embodiment, the mouthpiece 18 is movable relative to the housing 16 along the guide rails 40, 41. As illustrated in FIGS. 5-8, the mouthpiece 18 moves between a recessed position (FIGS. 5 and 6), where the mouthpiece 18 is retracted (e.g., hidden) inside the housing 16, to a non-recessed or exposed position (FIGS. 7 and 8), where the mouthpiece 18 is extended outside of the housing 16. The user utilizes the outer ring 56 to move the mouthpiece 18 between the recessed and the exposed position. As shown in FIG. 8, the outer ring 56 has a larger circumference than the housing 16. When the mouthpiece 18 moves to the recessed position, the outer ring 56 slides over part of the housing 16 to protect the display 44 and to inhibit dust and other particles from entering into the spirometer 12 through the vents 46. When the mouthpiece 18 moves back to exposed position, the outer ring 56 correspondingly moves upward and exposes the display 44 and the vents 46. The mouthpiece 18, on the other hand, has a circumference smaller than the circumference of the housing 16. Therefore, when the mouthpiece 18 moves to the recessed position, the mouthpiece 18 becomes recessed into the housing 16. As illustrated in FIG. 5, when the mouthpiece 18 is in the recessed position, the cover 20 fits around the housing 16 to cover the mouthpiece 18. The cover 20 prevents dirt and other particles from damaging the measurement module 22 inside the housing 16 and prevents contamination of the mouthpiece 18.

The guiderails 40, 41 guide the movement of the mouthpiece 18 relative to the housing 16 while the notches 42, 43 inhibit unintentional movement of the mouthpiece 18 between the retracted or recessed position and the exposed position. When the first and second flanges 58, 60 engage the first notch 42, the mouthpiece 18 is maintained in the recessed position. The user can then move the outer ring 56 upward to move the mouthpiece 18 from the recessed position back to the exposed position. In the illustrated embodiment, the guide rails 40, 41 are open ended on the top portion and the top of the guide rails 40, 41 do not include a securing mechanism. Therefore, if the mouthpiece 18 needs to be replaced (e.g., for washing), it is easily removed from the housing 16. In other embodiments, the guide rails 40, 41 include a top securing mechanism that is disengaged before the mouthpiece 18 is removed from the housing 16. In yet other embodiments, the mouthpiece 18 is not removable from the housing 16.

Figure 2A:
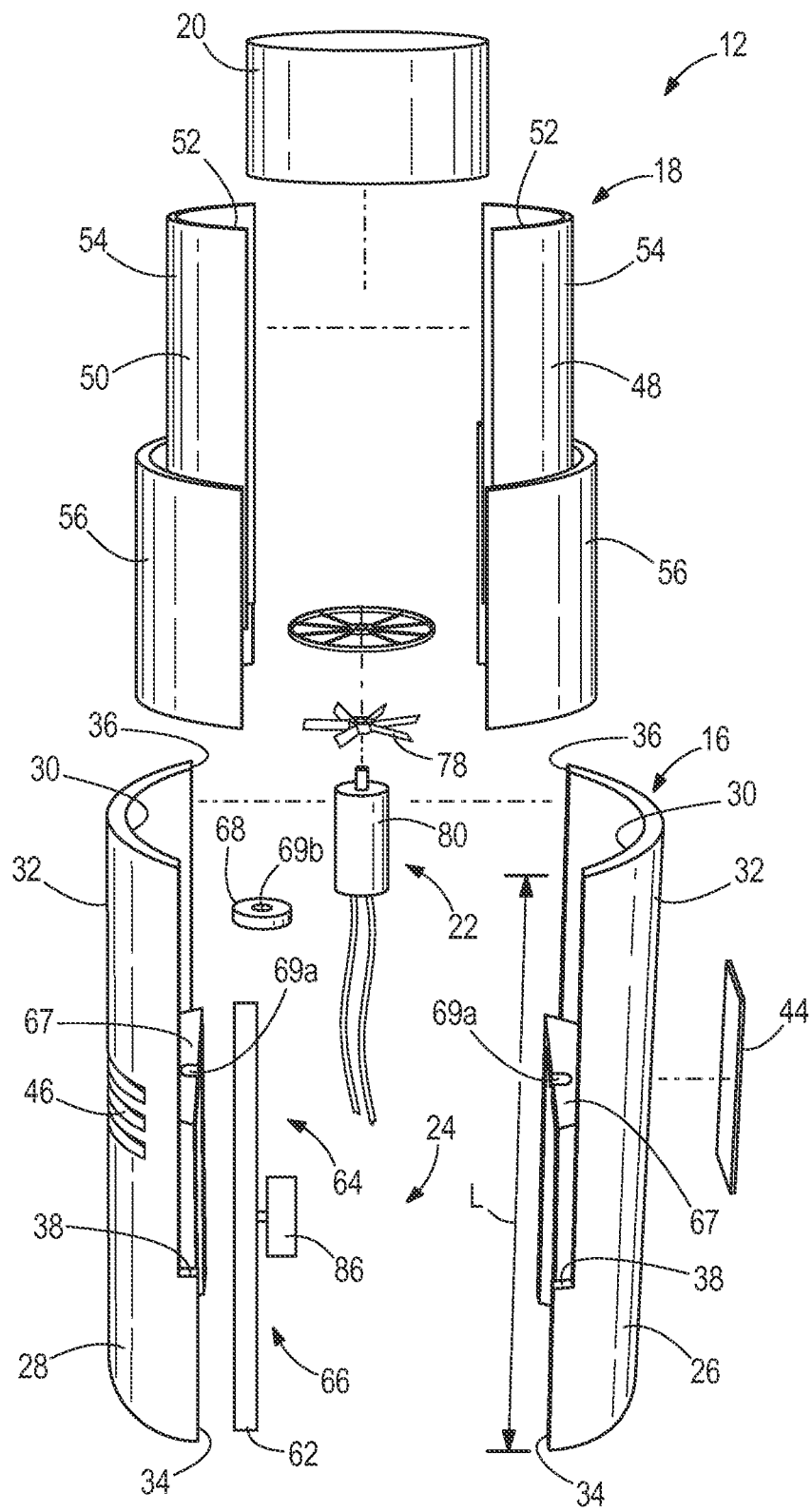
FIG. 2A is an exploded view of internal components of the spirometer of the system illustrated in FIG. 1.
Figure 2B:
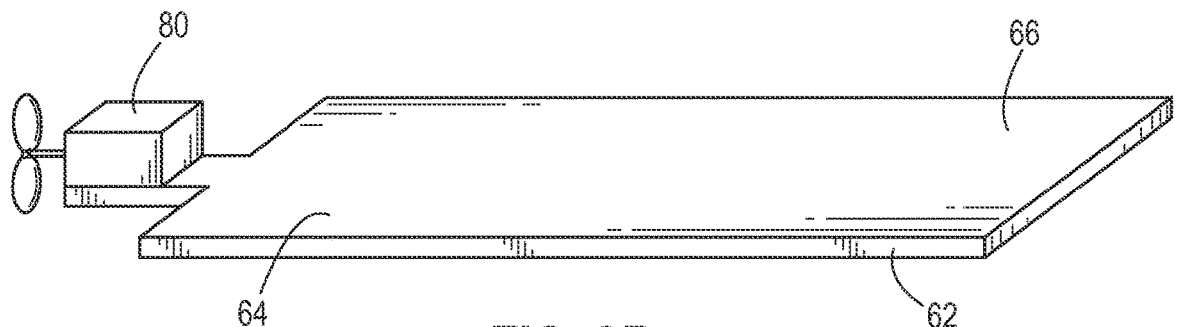
FIG. 2B illustrates a single circuit board of the spirometer.
Figure 2C:
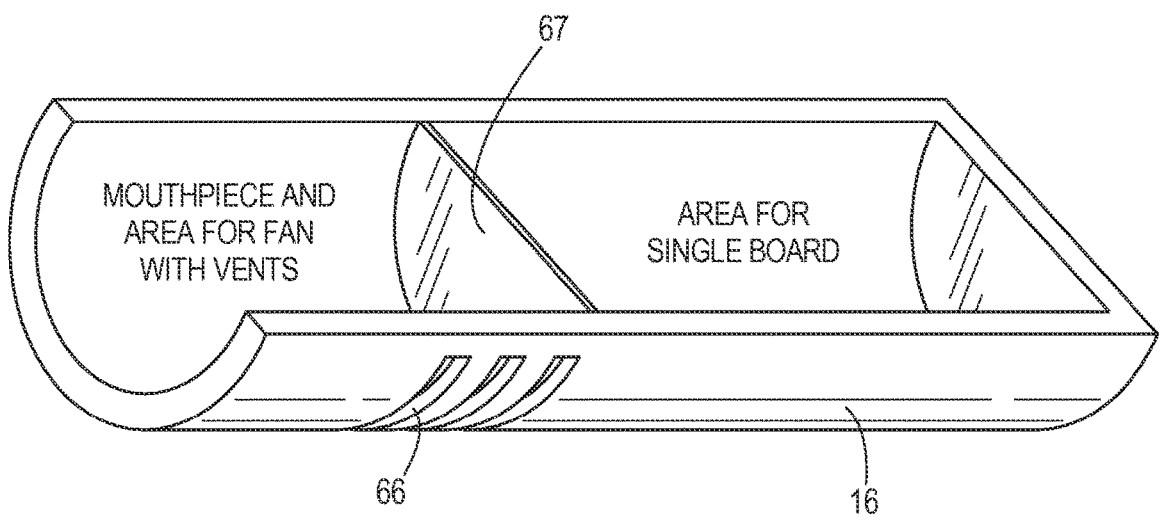
FIG. 2C illustrates a portion of the housing with a partition to protect the circuit board.
Figure 3:
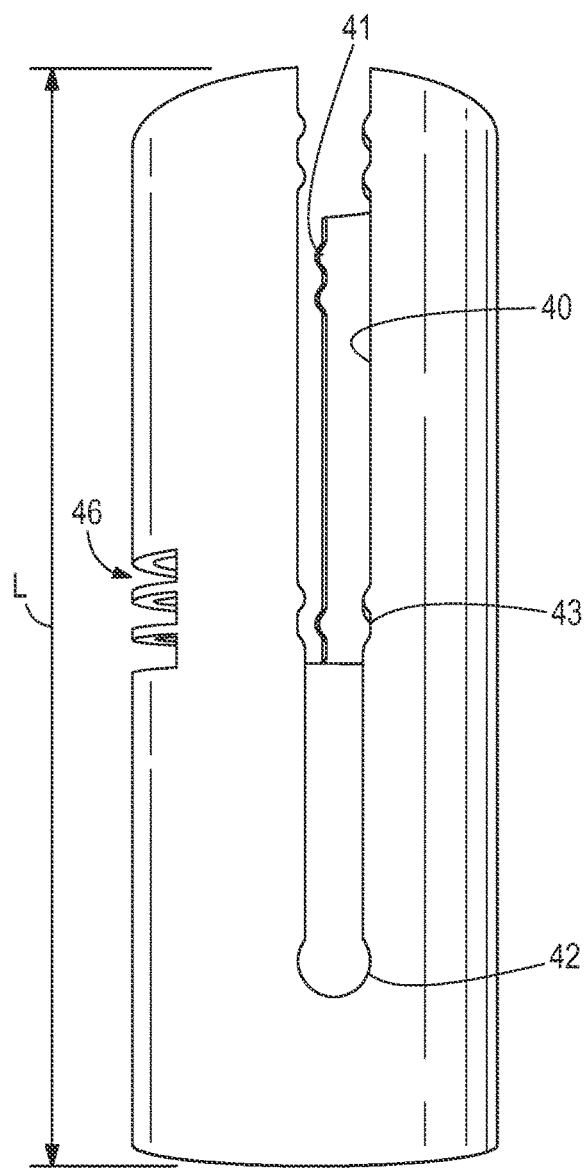
FIG. 3 shows the spirometer in a recessed position with a cover.

As shown in FIGS. 2A-C, the measurement module 22 and the processing module 24 are both positioned on a single printed circuit board 62. The single printed circuit board 62 is divided into a sensing portion 64 and a processing portion 66. The measurement module 22 is positioned on the sensing portion 64, while the processing module 24 is positioned on the processing portion 66. The housing 16 includes a partition 67 that protects the sensing portion 64, processing portion 66, and the processing module 24 from the user's expelled air and/or ambient air. In the illustrated embodiment, the printed circuit board 62 is protected by a protector 68. The protector 68 is positioned between the partition 67 and a motor 80. The motor 80 is positioned in a portion of the housing 16 that may be exposed to the expelled air from the user and/or the ambient air, but the partition 67 and the protector 68 maintain the printed circuit board 62 generally free from the environment (e.g., the user's expelled air and/or the ambient air). The partition 67 and the protector 68 each include a corresponding cavity 69a, 69b. The cavities 69a, 69b are aligned and allow connecting cables from the motor 80 to be connected to the sensing portion 64 of the circuit board 62. In the illustrated embodiment, the protector 68 includes a gasket. In other embodiments, the protector 68 can include a spacer to separate the single printed circuit board 62 from the expelled air from the user. In some embodiments, the protector 68 can be used to adjust the position of the measurement unit 22 (e.g., fan 78 and motor 80). Having the single circuit board 62 also allows for easier and less expensive manufacturing of the spirometer 12.

The measurement module 22 receives airflow from a user through the mouthpiece 18 and measures certain pulmonary parameters as well as other parameters associated with the user's breath or the ambient air (e.g., ambient air parameters). As shown schematically in FIG. 9, the measurement module 22 includes a main measurement unit 70, a humidity sensor 72, a temperature sensor 74, and a gas concentration sensor 76. In the illustrated embodiment, the main measurement unit 70 measures the amount of air and the speed of air expelled by the user to determine different pulmonary parameters corresponding to the user. In the illustrated embodiment, the main measurement unit 70 includes a fan 78 and a motor 80 (e.g., a turbine). When a user blows air into the mouthpiece 18, the funnel shape of the mouthpiece 18 guides the user's breath into the fan 78. The fan 78 turns in response to the air blown in by the user. The fan 78 is coupled to a shaft of the motor 80, which causes the motor 80 to also turn when the fan 78 turns. As the fan 78 and the motor 80 turn, the motor 80 generates an electrical quantity. In the illustrated embodiment, the motor 80 generates a voltage indicative of one or more pulmonary parameters corresponding to the user. In other embodiments, the measurement unit 70 may generate a different electrical quantity such as, for example, a current, a magnetic field, and the like. The electrical quantity is then sent to the processing module 24.

The humidity sensor 72 measures the amount of moisture in the air expelled by the user or in the ambient air. Analogously, the temperature sensor 74 measures the relative temperature of the user's breath and/or the ambient air. In the illustrated embodiment, the gas concentration sensor 76 measures the concentration of nitric oxide in the air expelled by the user. In other embodiments, the gas concentration sensor 76 may measure the concentration of other gases. In other embodiments, the measurement module 22 includes more than one gas concentration sensor 76 to measure the concentration of different gases. The output from each of the sensors is forwarded to the processing module 24. In some embodiments, the spirometer 12 may include more or less sensors than those described in this example.

Figure 9:
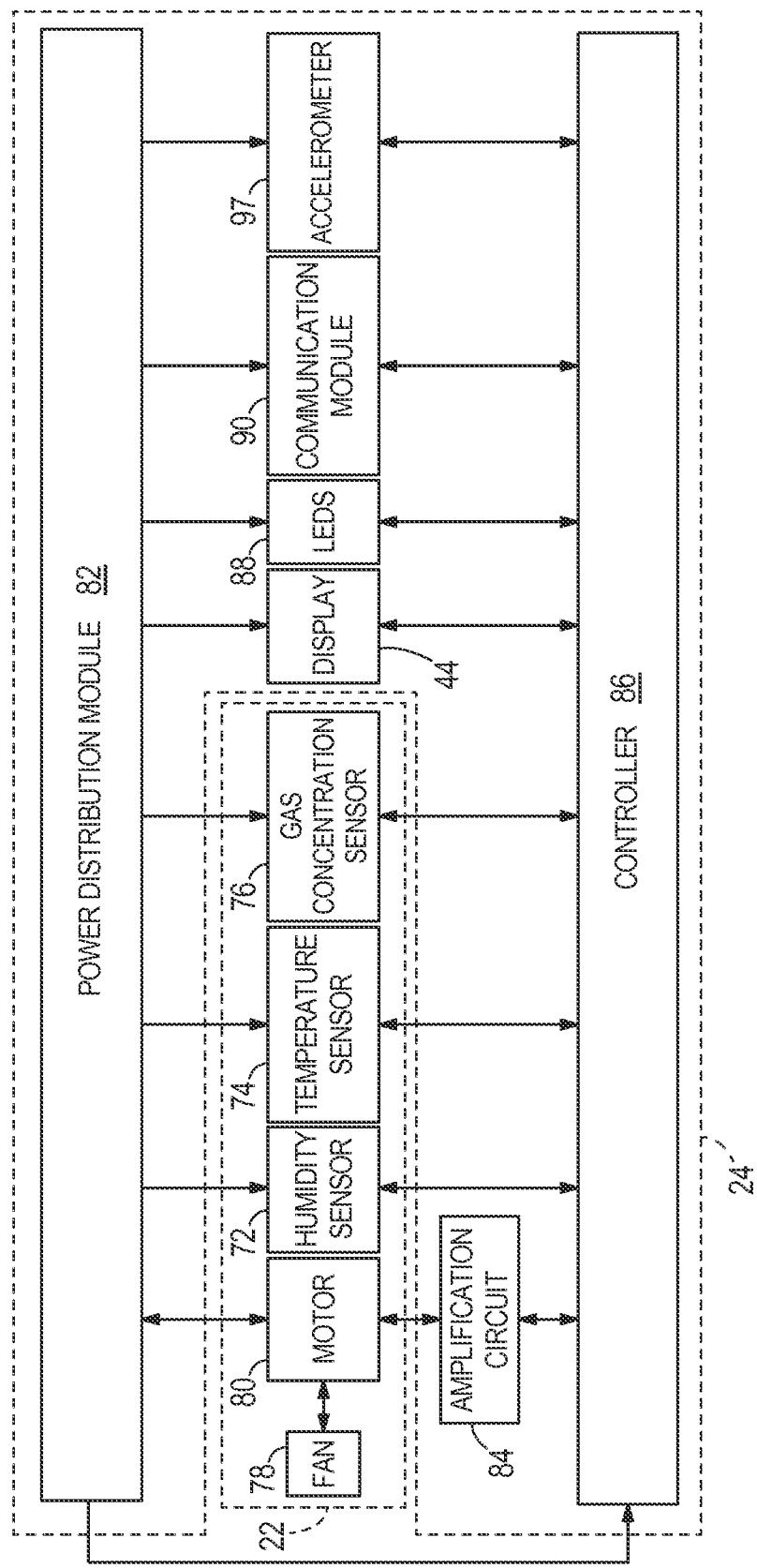
FIG. 9 schematically illustrates a measurement module and a processing module of the spirometer according to one embodiment of the invention.
Figure 10:
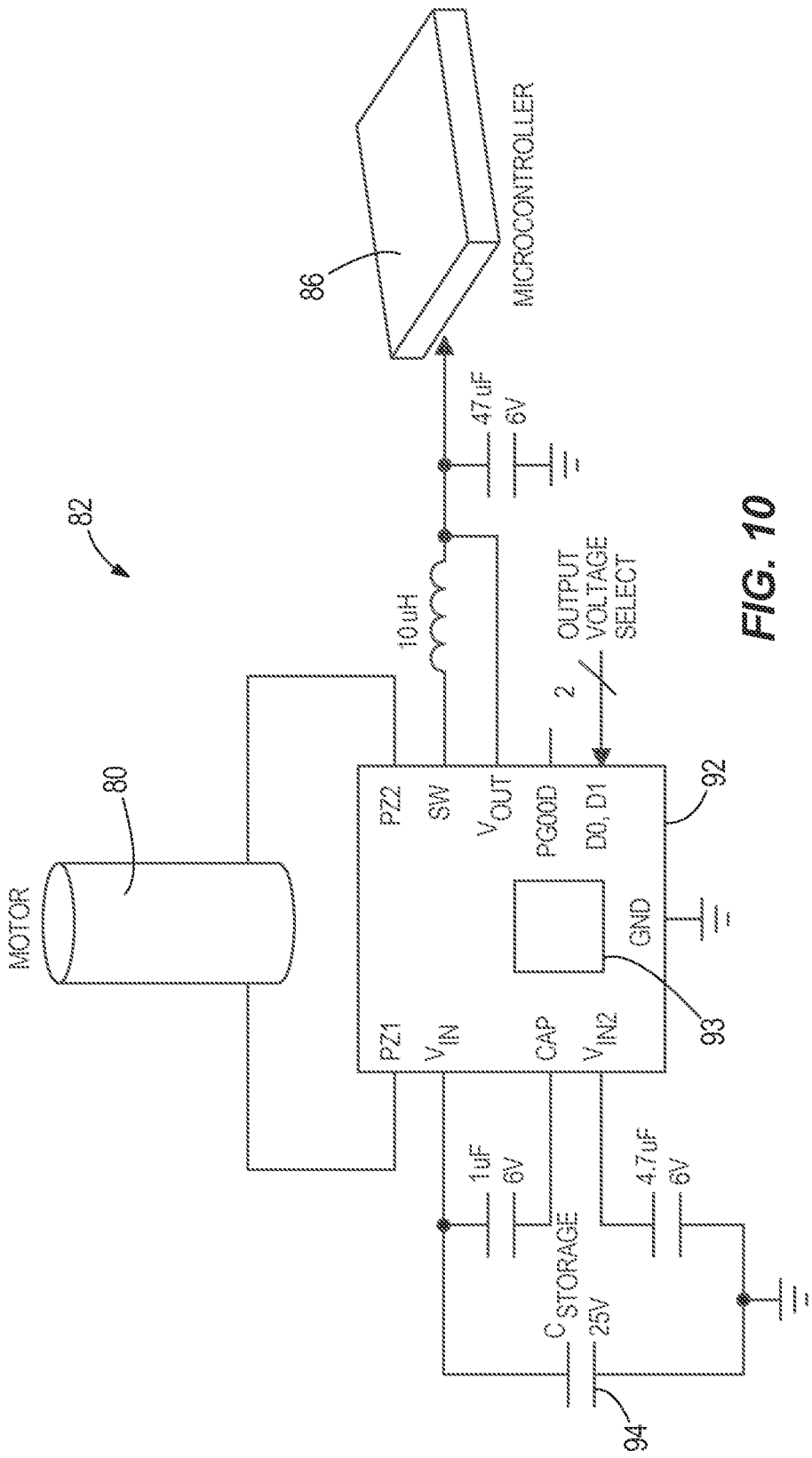
FIG. 10 is a schematic diagram of a power distribution module of the spirometer according to one embodiment of the invention.

As also shown schematically in FIG. 9, the processing module 24 includes a power distribution module 82, an amplification circuit 84, a controller 86, the display 44, LEDs 88, and a communication module 90. As shown in FIG. 10, the power distribution module 82 includes an energy harvester 92 that provides power to the rest of the electrical components of the spirometer such as, for example, the display 44, the LEDs 88, the controller 86, etc. In the illustrated embodiment, the energy harvester 92 receives power from the motor 80 of the main measurement unit 70. When the fan 78 and motor 80 is turned by the user's breath, the motor 80 generates a voltage waveform. The energy harvester 92 includes a buck converter that receives the voltage waveform from the motor 80 and transfers at least some of the power received from the motor 80 to the other electrical components of the spirometer 12. The buck converter transfers some of the power to the controller 86 in regulated amounts. Therefore, the spirometer 12 can be powered entirely by the user's breath. In other words, one way to harvest energy is to harvest energy from the airflow of the user's breath. The airflow of the user's breath turns the fan, which turns the motor generator, which produces electricity. In some embodiments, the energy harvester 92 includes a commercially available integrated circuit specifically manufactured for receiving and harvesting power.

In some embodiments, the energy harvester 92 also includes an external energy sensing and converting device. The energy sensing and converting device 93 receives energy from the environment, the energy detected by the energy sensing and converting device 93 is then used by the energy harvester 92 to provide electrical energy to the other components of the spirometer 12. The energy sensing and converting device 93 can include a heat sensor that detects heat energy, a light sensor that detects light energy, and the like. In some embodiments, the energy sensing and converting device 93 detects energy from motion using a piezoelectric sensor or through electromagnetics by moving a coil or a magnet coupled to each other to generate a voltage or a current. In other embodiments, the energy sensing and converting device 93 detects wind energy (energy from the motion of air). This wind energy sensing and converting device 93 may be separate from the fan 78 and the motor 80 described as part of the measurement unit 70. Therefore, the spirometer 12 can receive energy from different sources of energy without needing a battery.

Figure 11:
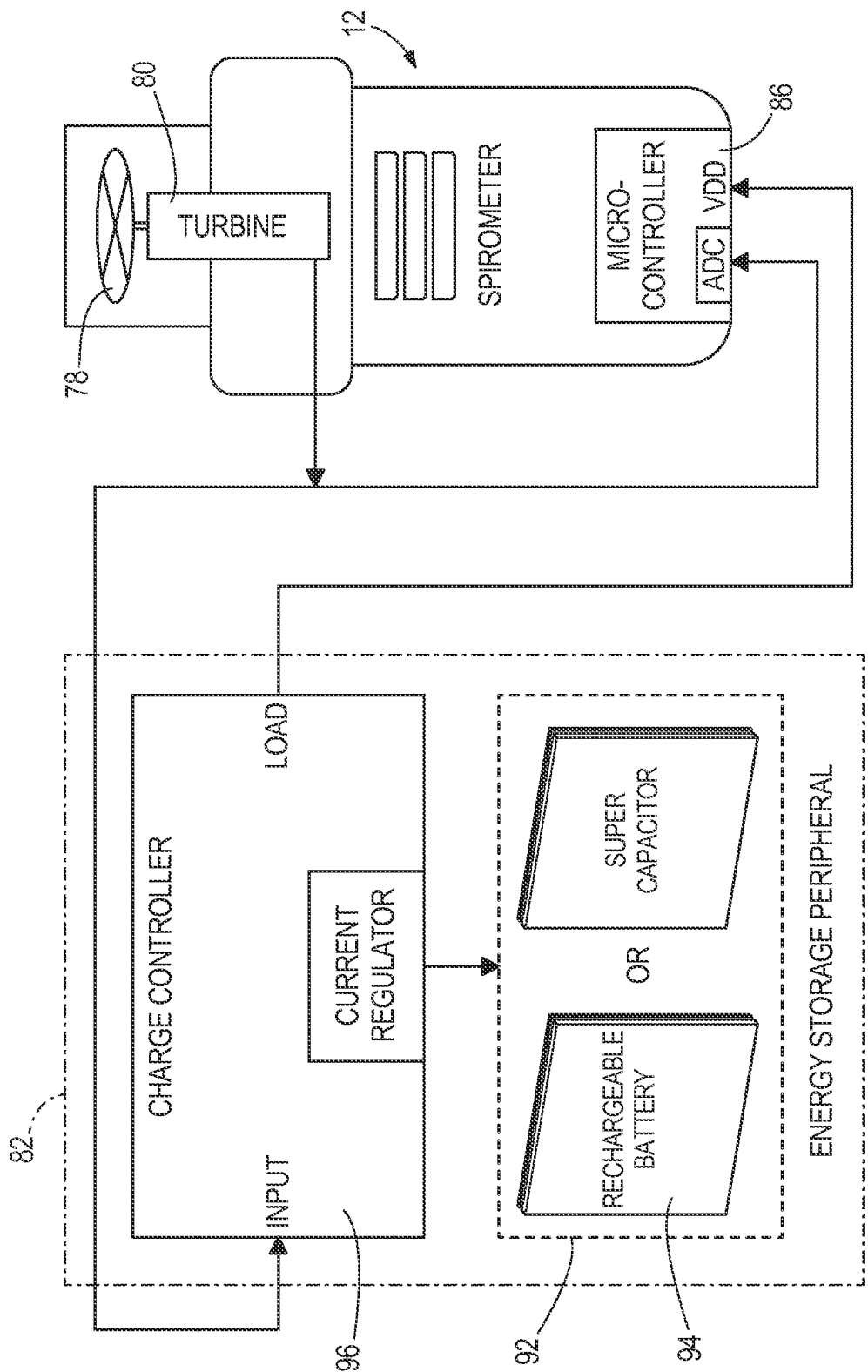
FIG. 11 is a schematic diagram of the spirometer.

As shown in FIG. 10, the power distribution module 82 also includes an energy storage device 94. The energy storage device 94 can store a portion of the power generated and conditioned by the energy harvester 92 for later use. In the illustrated embodiment, the energy storage device 94 includes a high-capacity capacitor. In other embodiments, the energy storage device 94 includes a rechargeable battery, such as a lithium polymer battery. In such embodiments, additional circuitry to further condition the power received from the motor 80 to charge the battery may be included in the power distribution module 82. As shown schematically in FIG. 11, the energy harvester 92 is coupled to a charge controller 96 that conditions the energy from the energy harvester 92, and transfers the conditioned energy to the energy storage device 94. The energy storage device 94 then transfers power to the controller 86 as necessary to operate the spirometer 12. In some embodiments, the spirometer 12 may be powered entirely by the user's breath. In other embodiments, the energy harvester 92 extends the life of a rechargeable battery by providing an additional power input.

Figure 12:
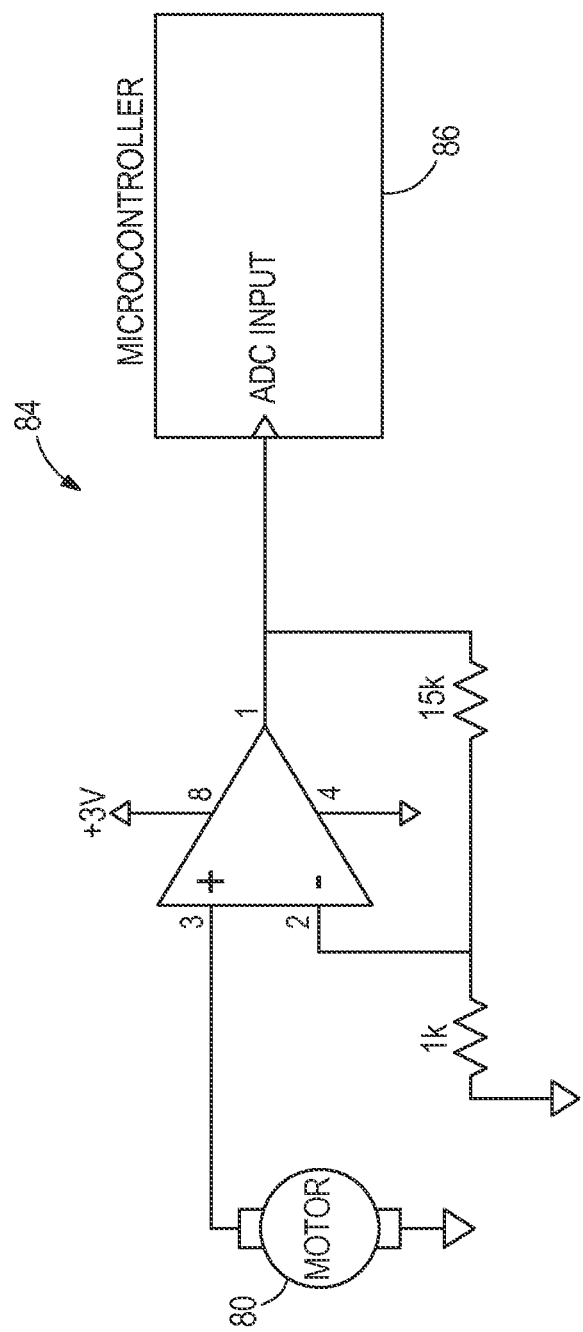
FIG. 12 schematically illustrates an amplification circuit of the spirometer according to one embodiment of the invention.

Referring back to FIG. 9, the amplification circuit 84 is coupled between the motor 80 and the controller 86. FIG. 12 illustrates one embodiment of the amplification circuit 84. The amplification circuit 84 receives at least one electrical quantity from the measurement module 22. In the illustrated embodiment, the amplification circuit 84 receives the electrical quantity from the motor 80. The amplification circuit 84 then outputs a correspondingly larger voltage to the controller 86 for further analysis and processing. In the illustrated embodiment, the voltage output from the motor 80 is in the order of millivolts, and the output from the amplification circuit 84 is in the order of volts. FIG. 12 illustrates a specific implementation of the amplification circuit 84. It should be understood that using components of different values can achieve the same or significantly similar functionality as the illustrated amplification circuit. Although FIG. 9 only illustrates the amplification circuit 84 coupled to the motor 80, some of the sensors 72, 74, 76 can also be coupled to an amplification circuit 84 to provide a generally greater output to the controller 86.

As illustrated in FIG. 9, the controller 86 is coupled to the power distribution module 82, the amplification circuit 84, the display 44, the LEDs 88, the measurement module 22, and the communication module 90. In some embodiments the controller 86 is a Texas Instruments' CC2540 microcontroller. However, the controller 86 can include standard components, such as a processor, non-transitory computer-readable medium, and an input/output interface (e.g., for communicating with the amplification circuit 84, the display 44, and the LEDs 88). The computer-readable medium stores instructions executable by the processor to perform particular functionality as described below. Accordingly, functionality described as being performed by the controller 86 can be performed by executing instructions stored in the computer-readable medium. Also, in some embodiments, the controller 86 includes an application specific integrated circuit (ASIC) in addition to or as an alternative to the processor and the computer-readable medium.

The controller 86 is configured to receive an amplified electrical quantity from the amplification circuit 84. For example, the amplification circuit 84 provides the controller 86 with a voltage waveform indicative of at least one pulmonary parameter of the user. The controller 86 is configured to determine a peak expiratory flow measurement and a forced expiratory volume measurement based on the received voltage waveform. The peak expiratory flow is the maximal flow (or speed) achieved during a forced expiration after full inspiration. The forced expiratory volume is the volume of air that can forcibly be blown out in a predetermined time, such as approximately one second, after full inspiration. In other embodiments, the controller 86 can determine other pulmonary parameters, such as forced expiratory flow, forced vital capacity, or maximum voluntary ventilation.

Figure 13A:
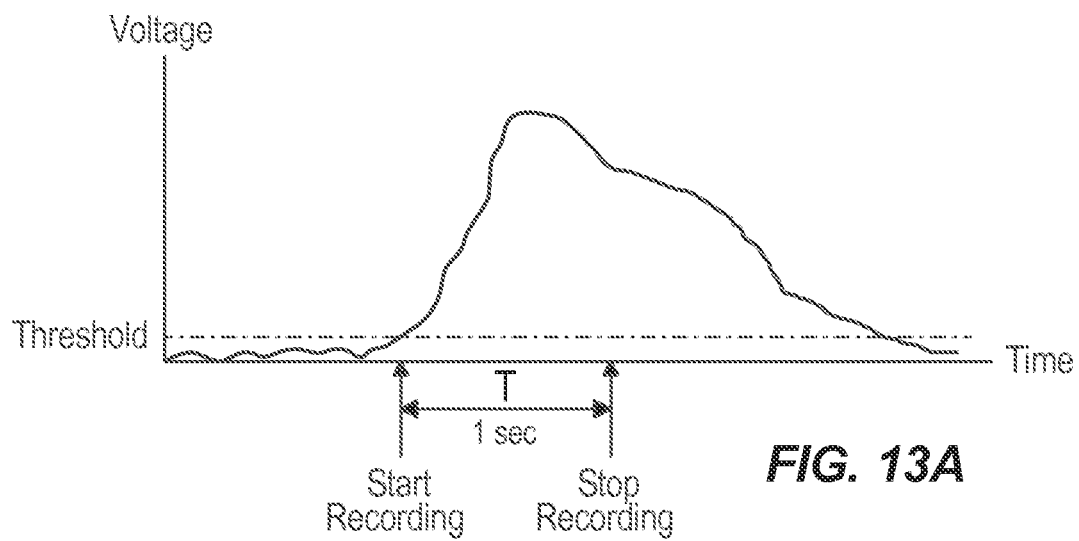
FIG. 13A is a graphical illustration of a voltage signal generated by the spirometer.
Figure 13B:
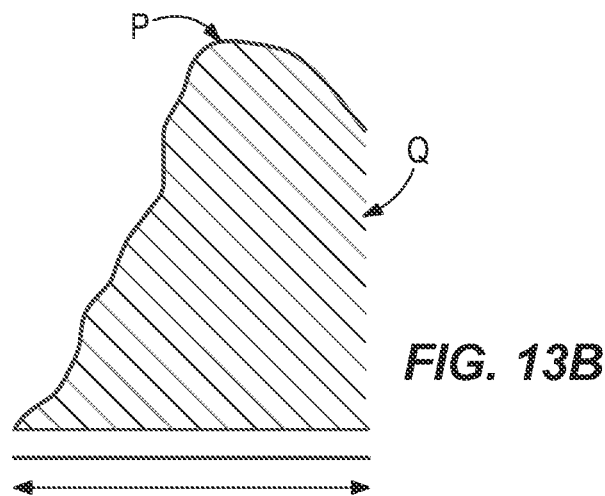
FIG. 13B is an enlarged graphical illustration of a portion of the voltage signal shown in FIG. 13A analyzed by the spirometer.

FIGS. 13A-B illustrate an exemplary voltage waveform generated by a user. FIG. 13A illustrates the voltage waveform received by the controller 86. The waveform of FIG. 13A corresponds to the volume of air exhaled by the user as a function of time. In particular, the controller 86 can be configured to measure and record a voltage from the amplification circuit 84 indicative of air volume for a predetermined time, such as approximately one second. In the illustrated embodiment, the controller 86 begins recording the voltage waveform once the voltage exceeds a predetermined voltage (e.g., 0.3V). Once the voltage has been recorded for the predetermined time (e.g., period T shown in FIG. 13A), the controller 86 determines the maximum point (P) of the recorded voltage waveform (indicative of the peak expiratory flow) and calculates the forced expiratory volume in the predetermined time (e.g., by calculating the area underneath the waveform for the predetermined time Q), as shown in FIG. 13B.

The controller 86 is also configured to transmit signals to the display 44 to cause the display 44 to display an indication (e.g., the measured value) of the peak expiratory flow and/or the forced expiratory volume to the user. In some embodiments, the controller 86 is also configured to activate one or more LEDs 88 based on the measurements. In the illustrated embodiments, the controller 86 also determines whether the measured pulmonary parameters (e.g., the peak expiratory flow and/or the forced expiratory volume) fall within an acceptable range. The controller 86 resorts to a memory of the controller 86 to determine what the acceptable range is. For example, the controller 86 determines whether the measured peak expiratory flow or the measured forced expiratory volume are within a normal range by comparing the measured pulmonary parameters to a low threshold, a high threshold, or a combination thereof. The controller 86 then illuminates the LEDs 88 based on the determination of whether the measured pulmonary parameters are within the normal ranges. For example, if the peak expiratory flow is below a predetermined threshold (i.e., if the peak expiratory flow is too low), the controller 86 can be configured to turn on an LED 88 in a first color, for example, red. In contrast, if the peak expiratory flow is within a predetermined range (e.g., a normal range associated with the user), the controller 86 can be configured to turn on an LED 88 in a second color, for example, green. If the peak expiratory flow is in between the low end of the predetermined range and the predetermined threshold, the controller 86 can be configured to turn on an LED 88 in a third color, for example, yellow.

The communication module 90 is coupled to the controller 86 and is configured to communicate with the electronic device 14. In some embodiments, such as in the implementation of the Texas Instruments' CC2540 microcontroller, the communication module 90 is built into the controller 86. The communication module 90 is configured to transfer data obtained through the measurement module 22 from the spirometer 12 to the electronic device 14. The communication module 90 can communicate with the electronic device 14 with a wired connection, a wireless connection, or both. In some embodiments, the communication module 90 uses Bluetooth 2.0 (or Bluetooth Low Energy (LE)) technology to communicate with the electronic device 14. For example, the communication module 90 can include a Bluetooth 2.0 module. The Bluetooth 2.0 module may include an integrated circuit having, for example, four pins (e.g., power, ground, and data communication lines). In other embodiments, the communication module 90 may use the Bluetooth (LE) protocol to communicate with the electronic device 14. As noted above, the communication module 90 may be integrated into the controller 86. In these embodiments, the only external feature of the communication module 90 can be an RF matching circuit and an antenna. In other embodiments, the communication module 90 may use other forms of wireless communication, such as RFID wireless communication, cellular connections, and/or far-range wireless communication (e.g., Wi-Fi). In some embodiments, a wired connection can be used between the spirometer 12 and the electronic device 14 (e.g., a USB connection or a headphone connection) in addition to or as an alternative to a wireless connection.

If the communication module 90 detects a compatible electronic device 14 nearby (e.g., within a predetermined distance from the spirometer 12), the communication module 90 sends a wireless message including the measurement data (e.g., measured pulmonary parameters and/or ambient air data) to the electronic device 14 for storage and, in some embodiments, further analysis. If the communication module 90 does not detect an electronic device 14 nearby, the measurement data is stored on the spirometer 12 for later transfer. In some embodiments, the spirometer 12 searches for a compatible electronic device 14 immediately after powering on to transmit previously stored measurement data. It should be understood that the spirometer 12 is usable with or without an electronic device 14.

In some embodiments, the spirometer 12 conserves energy by switching operation between an awake mode and a sleep mode. In the sleep mode, the measurement module 22 and the processing module 24 shuts down unnecessary components. In other words, the measurement module 22 is inactive while the spirometer 12 is in the sleep mode. The spirometer, therefore, has a lower power consumption since there is little to no expectation of receiving a measurement from the measurement module 22. In the awake mode, the measurement module is active and measures pulmonary parameters of the user. In the awake mode, the processing module 24 is fully operational and receives the electrical quantities from the measurement module 22.

In the illustrated embodiment, the processing module 24 also includes an accelerometer 97 coupled to the controller 86. The processing module 24 can switch from the sleep mode to the awake mode by monitoring signals from the accelerometer 97. The controller 86 monitors the signals from the accelerometer 97 to determine when the spirometer 12 is moved (e.g., to begin use of the spirometer). When the processing module 24 (e.g., the controller 86) determines that the spirometer 12 is moved, the processing module 24 exits the sleep mode and enters the awake mode to receive measurements from the measurement module 22. In other embodiments, other methods and/or sensors may be used to switch the processing module 24 from the sleep mode to the awake mode. For example, the spirometer 12 may include a switch movable between a first position and a second position. When the switch is in the first position, the processing module 24 is in the sleep mode, but when the switch is in the second position, the processing module 24 enters the awake mode. In other embodiments, the processing module 24 may exit the sleep mode and enter the awake mode when the user blows into the spirometer 12. In such embodiments, the controller 86 monitors the signals from the motor 80.

Figure 14:
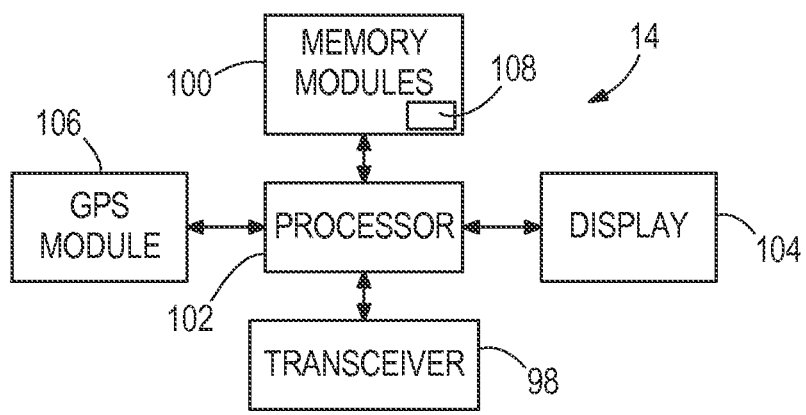
FIG. 14 schematically illustrates an electronic device included in the system of FIG. 1.

In the illustrated embodiment, the electronic device 14 includes standard components found in a cellular telephone, a smart phone, and/or a tablet computer. For example, as shown in FIG. 14, the electronic device 14 includes a transceiver 98, one or more memory modules 100, a processor 102, a display 104 (which can include a touchscreen), and a GPS module 106. The electronic device 14 can be, for example, a smart phone, a smart watch, a tablet computer, a laptop computer, or other computing device that includes the transceiver 98 to receive and send information to other electronic devices such as, the spirometer 12.

The memory modules 100 includes non-transitory computer readable medium. The non-transitory computer readable medium includes, for example, random access memory "RAM" and/or read-only memory ("ROM"). The processor 102 retrieves instructions from the memory modules 100 and executes the instructions to perform particular functionality. The processor 102 can also retrieve and store data to the memory modules 100 as part of executing the instructions. For example, in the illustrated embodiment, the memory modules 100 store a pulmonary analysis application 108. In other embodiments, the electronic device 14 connects to a remote memory (e.g., included in a server accessible over the Internet) to access and interact with the pulmonary analysis application 108. In yet other embodiments, some aspects of the pulmonary analysis application 108 are hosted by the electronic device 14 and other aspects of the pulmonary analysis application 108 are remotely accessible.

The controller 86 generates a graphical user interface (GUI) according to instructions from the pulmonary analysis application 108. The GUI presents information on the display 104 in an understandable manner. FIGS. 15A-F illustrate exemplary screenshots of the pulmonary analysis application 108 and features available to the user through the pulmonary analysis application 108. For example, a user can use the pulmonary analysis application 108 to view past measurements in a daily, weekly, monthly, or annual form for current and future use, navigate between measurement graphs, and journal entries. Additionally, the pulmonary analysis application 108 includes instructions and data executable by the processor 102 to analyze respiratory data and other measurements received from the spirometer 12. In particular, the pulmonary analysis application 108 can store the measurement data, graph the measurement data, correlate the measured data to specific treatment instructions, communicate the measurement data to a physician or medical care facility, and/or associate the measurement data with a particular patient. FIG. 15A illustrates a homepage available to the user to navigate the pulmonary analysis application 108 and access different features. As shown in FIG. 15A, the homepage includes several digital buttons to aid the user in navigating the pulmonary analysis application 108. The homepage includes a pair device button 110, a journal button 116, a dashboard button 112, a graph button 118, a help button 120, and a settings button 114. In other embodiments, the homepage may display more or less digital buttons and may allow the user to navigate the pulmonary analysis application 108 differently.

The pair device digital button 110 allows the electronic device 14 to pair with the spirometer 12 to exchange pulmonary data. FIG. 15B illustrates an exemplary screenshot providing instructions to a user for pairing the electronic device 14 with the spirometer 12. In some embodiments, the electronic device 14 sends a pairing signal to the spirometer 12 upon launching the pulmonary analysis application 108. In other embodiments, a certain pairing procedure is executed by the spirometer 12 before pairing to the electronic device 14. For example, in some embodiments, confirmation to pair is requested on the spirometer 12 to inhibit the spirometer 12 from pairing to a wrong electronic device by accident. Once the electronic device 14 and the spirometer 12 are paired, the pulmonary analysis application 108 is configured to receive pulmonary and/or ambient air measurement data.

Figure 15C:
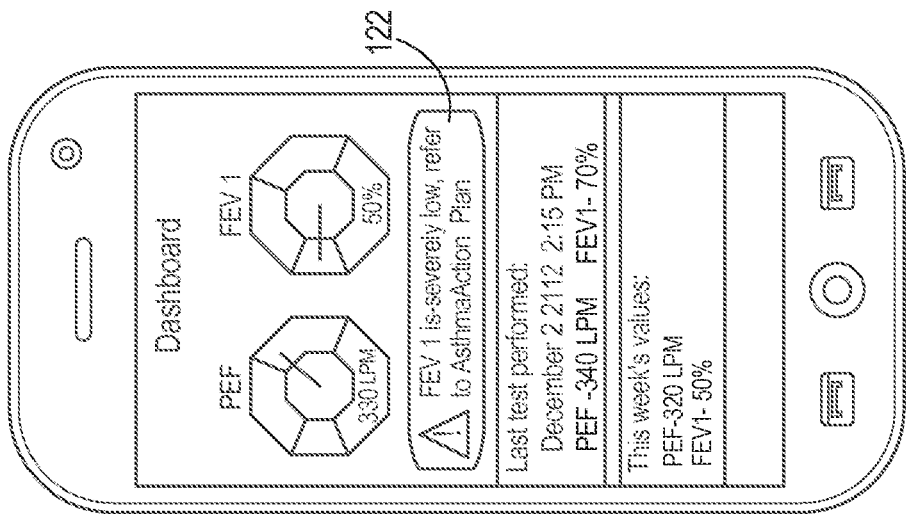
FIGS. 15A-15F illustrate exemplary screenshots of a graphical user interface generated by the electronic device.
Figure 15B:
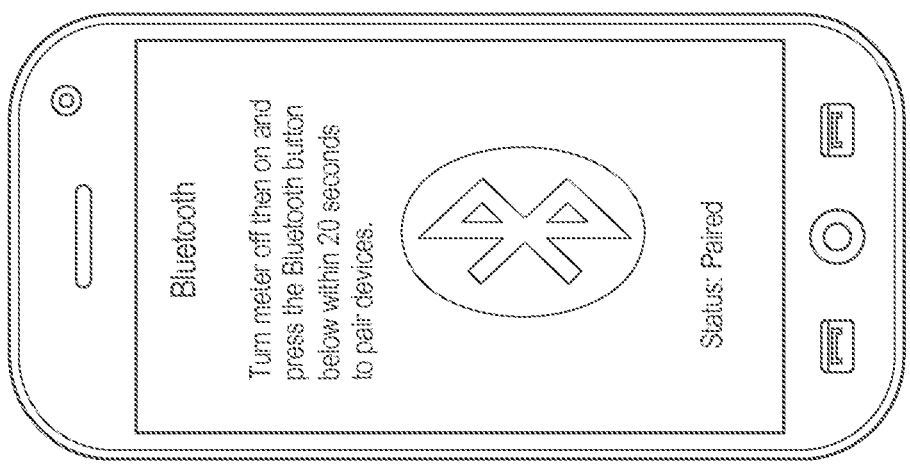
Figure 15A:
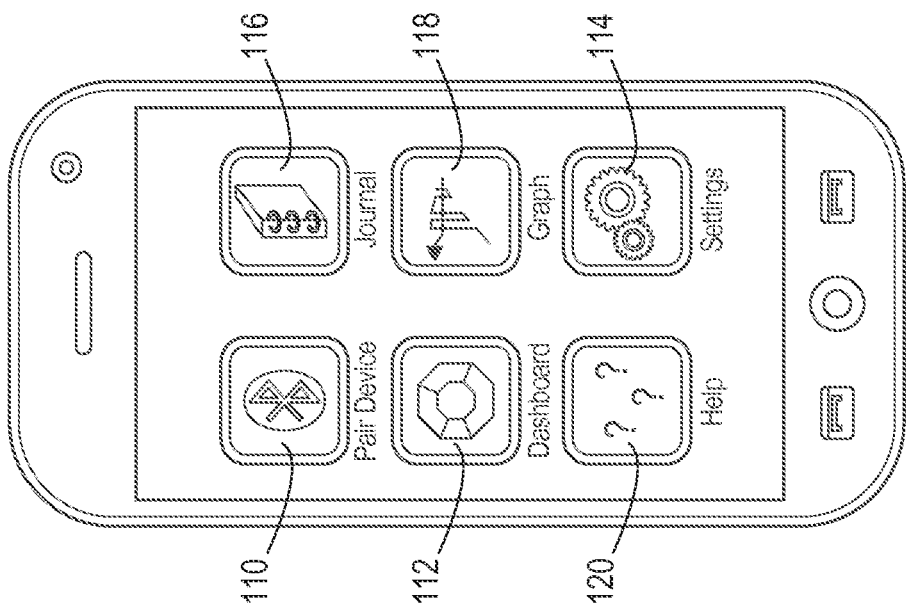

The dashboard digital button 112 presents to the user the most recent pulmonary measurement information, as shown in FIG. 15C. As described above, the pulmonary analysis application 108 stores algorithms and methods for analyzing the measurement data received from the spirometer 12. The pulmonary analysis application 108 may compare the received pulmonary measurements to predetermined threshold(s) to assess the pulmonary health of the user. As shown in FIG. 15C, the pulmonary analysis application 108 illustrates whether the pulmonary parameters are within range with different indicators. In the illustrated example, the forced expiratory volume of the user is severely low. The pulmonary analysis application 108 generates an alert message 122 to inform the user that at least one of the measured pulmonary parameters is outside the expected range. In some embodiments, if the pulmonary measure is severely low or high, the pulmonary analysis application 108 displays a specific treatment action to be performed by the user according to an action plan. For example, when a pulmonary measurement falls outside of the user's normal range (i.e., the peak expiratory flow is too low), the pulmonary analysis application 108 can be configured to determine a treatment action. The treatment action can be one of the stored user parameters. Therefore, the treatment action can vary for the particular user and his/her own pulmonary health treatment plan. The treatment action can include using an inhaler, ceasing physical activity, consuming a particular medicine or controlled substance, calling a physician, informing a care provider, removing the user from a contaminated environment, and the like. In some embodiments, the pulmonary analysis application 108 sends a wireless alert message to a second electronic device to inform a family member or professional care provider of the abnormal pulmonary parameter. As shown in FIG. 15C, the dashboard screen may also show additional information such as past measurements, scheduled tests, and the like.

The pulmonary analysis application 108 is able to determine whether the measured pulmonary parameters fall outside normal ranges by comparing the received pulmonary and/or ambient air information from the spirometer 12 to stored threshold(s) and ranges. In the illustrated embodiment, the threshold and/or ranges are customizable for each user. In the illustrated embodiment, the threshold and/or ranges are based on a calculated average of the user's previous pulmonary parameter measurements. For example, the pulmonary analysis application 108 determines that the user's measured pulmonary parameter is within a normal range when the measured pulmonary parameter is ±5% of the calculated average of the user's previous pulmonary parameter measurements. In a similar manner, the pulmonary analysis application 108 determines that the user's measured pulmonary parameter is significantly low when the measured pulmonary parameter is 80% of the calculated average of the user's previous pulmonary parameter measurements. As explained, in the illustrated embodiment, the thresholds and/or ranges used to analyze the pulmonary parameters are based on a percentage and/or portion of the user's average pulmonary measurements. In other embodiments, the threshold and/or ranges are set by a professional care provider and are not based on the user's previous pulmonary parameter measurements.

The settings digital button 114 guides the user to a screen to change the pulmonary parameter thresholds. As shown in FIG. 15D, the settings screen includes three different regions for each pulmonary parameter. For example, if the forced expiratory volume (FEV) is above 94%, the user's pulmonary health is not currently at risk. However, if the forced expiratory volume (FEV) is below 86% (e.g., of a predetermined threshold), the user is at some risk of adverse pulmonary health, and if the forced expiratory volume (FEV) is below 65%, the user is at significant risk of an adverse pulmonary condition and/or reaction. As shown in FIG. 15D, the user can also customize the ranges associated with the peak expiratory flow corresponding to the user. In the illustrated embodiment, the user can also set reminders on the pulmonary analysis application 108. The user can set reminder to, for example, alert the user when another pulmonary test using the spirometer 12 should be performed. The reminder can be set to reoccur according to a specified frequency. In other words, the electronic device 14 can periodically (e.g., according to a predetermined schedule) alert the user to user the spirometer 12. The user can also set reminders for other purposes (e.g., to track amount of physical activity).

The pulmonary analysis application 108 can be customized for each user. For example, normal peak flow and expiratory volume measurements vary from person to person. Therefore, to determine if the respiratory measurements for a particular user fall within his/her normal range, the pulmonary analysis application 108 can be programmed for the user's particular normal range (the range can be initially determined by a physician during a visit with the user). For example, the pulmonary analysis application 108 can be configured to access stored parameters for a particular user. The application 108 can access the stored parameters to determine a particular user's normal range and/or customized treatment instructions for the user. In some embodiments, the application 108 can prompt a user for identifying information (e.g., through an interface displayed on the display 104) and use the identifying information to access the stored parameters for the identified user. Accordingly, one instantiation of the application 108 can be used with multiple different users. It should be understood that the user parameters can be stored on the electronic device 14 and/or a server accessible by the electronic device 14 (e.g., through the transceiver 98).

The pulmonary analysis application 108 can also store previously received and analyzed pulmonary measurements. For example, the journal entry digital button 116 guides the user to a history of the user's previous measured pulmonary parameters. As shown in FIG. 15E, the pulmonary analysis application 108 can track different measured pulmonary parameters. The pulmonary analysis application 108 can also be configured to store metadata regarding the measurement data. For example, through the GPS module 106, a particular location can be associated with a particular measurement. A time and a date can also be associated with a particular measurement (e.g., transmitted from the spirometer 12 and/or recorded by the application 108 upon receipt of the measurement data). In some embodiments, a user can input additional information regarding a particular measurement using the electronic device (e.g., using an interface displayed on the display 104). For example, a user can specify previous physical activity, location, medicines taken, or any other aspect that may have affected the particular measurement. In some embodiments, the pulmonary analysis application 108 can additionally or alternatively store information regarding the actions taken by the user after a particular measurement if the measurement was outside a predetermined range. For example, the user may want to look at how many asthma attacks he/she had in the previous year and what actions he/she took to remedy the situation. Such information can also be relayed to a particular physician and/or to a medical care facility and become incorporated into the user's medical record.

Figure 15F:
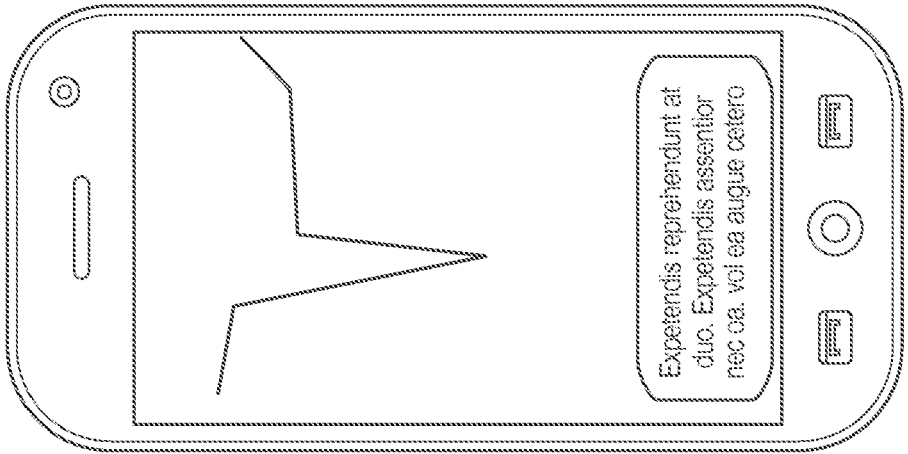
Figure 15E:
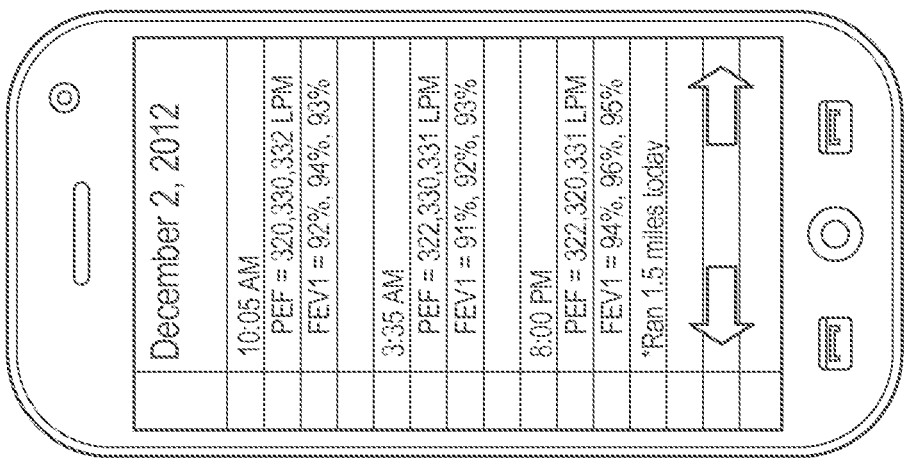
Figure 15D:
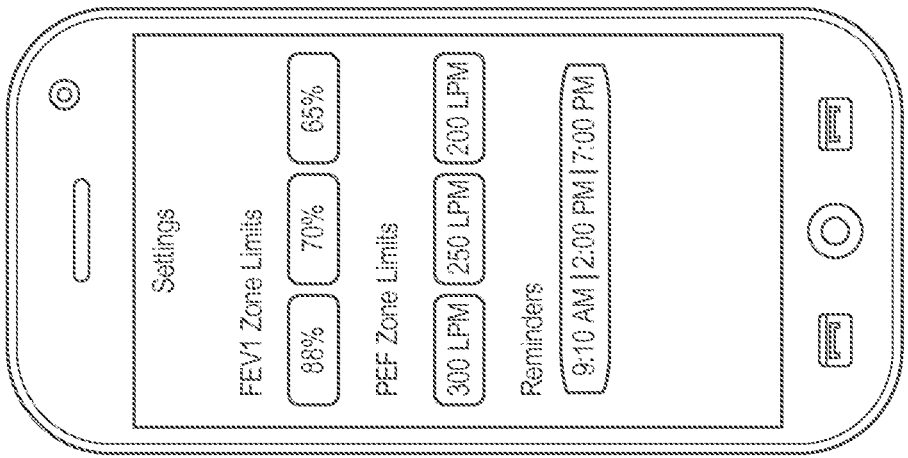

As shown in FIG. 15F, the user can also access information regarding past measured pulmonary parameters by pressing the graph digital button 118. The pulmonary analysis application 108 can illustrate the user's previously measured pulmonary parameters by plotting at least some of the stored measured pulmonary parameters. The graph in FIG. 15F illustrates that a particularly low pulmonary parameter was measured. The user can then use the journal entry button 116 to further investigate, for example, the actual reading for the pulmonary parameter, what actions, if any, were taken by the user in response to the abnormal measurement, whether or not information was forwarded to a physician or another care provider, etc.

The pulmonary analysis application 108 allows the user to gain a better understanding of his/her pulmonary health. Additionally, having different data logging features may significantly improve a user's ability to manage his/her pulmonary conditions (e.g., asthma). At the same time, the user's care providers remain informed and can provide higher quality care for the user.

Figure 16:
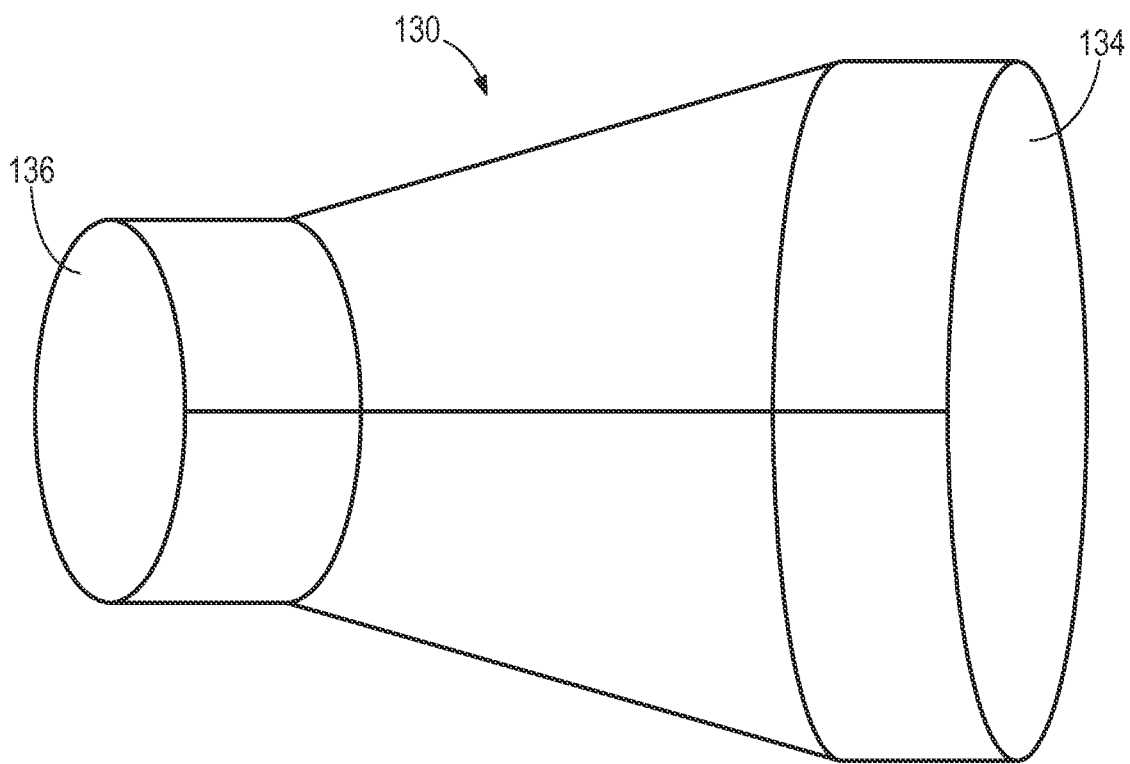
FIG. 16 illustrates an adapter for the spirometer.

In the illustrated embodiment, the spirometer 12 can additionally or alternatively be used with external filters and/or can be connected to external machines. As shown in FIG. 16, an adapter 130 can be coupled to either the mouthpiece 18 or the housing 16. The adapter 130 includes a first end 134 that couples to the spirometer 12 and a second end 136 that couples to an external component. The first end 134 has a generally elliptical shape to match the mouthpiece 18 or the housing 16. The second end 136, on the other hand, has a generally circular shape for coupling to an external circular filter or to other machinery. A circular connector is used more often for connecting to machines that measure pulmonary parameters. By attaching the adapter 130 to the spirometer 12, the spirometer 12 can remain portable, simple, and ergonomic, while still being connectable to more universal circular filters and/or machine connections.

Thus, embodiments of the invention provide, among other things, a portable, easy-to-use peak expiratory flow and forced expiratory volume spirometer 12 that is configured to communicate with an electronic device 14 to provide the user and a physician or medical care facility with up-to-date information regarding the user's respiratory health.

Various features and advantages of the invention are set forth in the following claims.

What is claimed is:

1. A spirometer comprising:
a housing;
a mouthpiece coupled to the housing;
a measurement unit including a fan and a motor, the measurement unit configured to receive air expelled by a user, and generate an electrical quantity corresponding to a peak expiratory flow or a forced expiratory volume based on the expelled air;
a controller supported by the housing, and configured to receive the electrical quantity from the measurement unit;
an energy harvester coupled to the measurement unit and the controller, the energy harvester configured to
receive energy from the measurement unit or an energy device,
store the received energy in an energy storage device, and
transfer the energy to the controller; and
an outer ring coupled to the mouthpiece, and wherein the outer ring covers a display when the mouthpiece is in the first position and the outer ring exposes the display when the mouthpiece is in the second position, and
wherein the housing includes a set of guiderails along a length of the housing, and wherein the mouthpiece is movable relative to the housing between a first position in which the mouthpiece is recessed within the housing, and a second position in which the mouthpiece is exposed outside the housing.

2. The spirometer of claim 1, wherein each guiderail of the set of guiderails includes a first notch to inhibit the mouthpiece from moving from the first position, and a second notch to inhibit the mouthpiece from moving from the second position.

3. The spirometer of claim 1, wherein the set of guiderails include includes a top portion that is open ended, and wherein the mouthpiece is removable from the housing through the top portion of the set of guiderails.

4. The spirometer of claim 1, wherein the mouthpiece is generally shaped as a funnel to receive the expelled air from the user.

5. The spirometer of claim 1, wherein the controller is configured to transmit a wireless message to an external electronic device regarding the peak expiratory flow or the forced expiratory volume.

6. The spirometer of claim 1, wherein the electrical quantity is a voltage corresponding to the peak expiratory flow or the forced expiratory volume.

7. The spirometer of claim 1, further comprising a removable cover configured to cover the mouthpiece.

8. The spirometer of claim 1, wherein the housing and the mouthpiece have a generally elliptical shape.

9. The spirometer of claim 1, further comprising an accelerometer supported by the housing and coupled to the controller, the accelerometer configured to detect motion of the spirometer.

10. The spirometer of claim 1, wherein the energy storage device includes a high-capacity capacitor.

11. The spirometer of claim 1, wherein the energy storage device includes a rechargeable battery.

12. The spirometer of claim 1, further comprising a charge controller coupled to the energy harvester, the charge controller configured to
receive energy from the motor or the energy device,
condition the energy from the motor or the energy device, and
transfer the conditioned energy to the energy storage device.

13. The spirometer of claim 1, wherein the spirometer is configured to operate in an awake mode in which the controller is active and the motor generates the electrical quantity corresponding to the peak expiratory flow or the forced expiratory volume, and sleep mode in which the controller is inactive, wherein the sleep mode has a lower power consumption than the awake mode.

14. The spirometer of claim 13, further comprising an accelerometer, wherein the spirometer is configured to switch from the sleep mode to the awake mode in response to receiving a signal from the accelerometer.

15. The spirometer of claim 1, wherein the display is coupled to the controller to display an indication of the peak expiratory flow or the forced expiratory volume.

16. The spirometer of claim 15, wherein the controller comprises a single circuit board, wherein the single circuit board includes a sensing portion and a processing portion, the sensing portion being coupled to the fan and the processing portion being coupled to the display.

17. The spirometer of claim 16, further comprising a gas sensor configured to detect a concentration of a gas in the expelled air, wherein the gas sensor being coupled to the sensing portion of the single circuit board.

18. The spirometer of claim 17, wherein the gas sensor is configured to detect a concentration of nitric oxide.

19. The spirometer of claim 16, wherein the sensing portion of the single circuit board is exposed to the expelled air, and wherein the processing portion is protected from the expelled air.

20. The spirometer of claim 15, wherein the display is configured to display different colors to indicate different conditions of a patient based on the measured peak expiratory flow or the forced expiratory volume.

21. A spirometer comprising:
a housing;
a mouthpiece coupled to the housing;
a fan supported by the housing;
a motor coupled to the fan, the mouthpiece configured to receive air expelled by a user, and thereby turn the fan and the motor to generate an electrical quantity corresponding to a peak expiratory flow or a forced expiratory volume based on the expelled air;
a controller supported by the housing, and configured to receive the electrical quantity from the motor; and
an energy harvester coupled to the motor and the controller, the energy harvester configured to
receive energy from the motor or an energy device,
store the received energy in an energy storage device, and
transfer the energy to the controller.
wherein the housing includes a set of guiderails along a length of the housing, and wherein the mouthpiece is slideable relative to the housing between a first position in which the mouthpiece is recessed within the housing, and a second position in which the mouthpiece is exposed outside the housing,
wherein the set of guiderails include a top portion that is open ended, and wherein the mouthpiece is removable from the housing through the top portion of the set of guiderails.

22. The spirometer of claim 21, wherein the mouthpiece is generally shaped as a funnel to receive the expelled air from the user.

* * * * *